United States Patent
Phillips

(10) Patent No.: US 10,932,931 B2
(45) Date of Patent: Mar. 2, 2021

(54) MEDICAL DEVICE DELIVERY SYSTEM INCLUDING A SUPPORT MEMBER

(71) Applicant: Medtronic Vascular, Inc., Santa Rosa, CA (US)

(72) Inventor: Shawn Phillips, Belle Plaine, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 101 days.

(21) Appl. No.: 15/919,973

(22) Filed: Mar. 13, 2018

(65) Prior Publication Data

US 2019/0282384 A1    Sep. 19, 2019

(51) Int. Cl.
*A61F 2/966* (2013.01)
*A61F 2/915* (2013.01)

(52) U.S. Cl.
CPC ............ *A61F 2/966* (2013.01); *A61F 2/915* (2013.01); *A61F 2002/91575* (2013.01); *A61F 2002/9665* (2013.01); *A61F 2250/0018* (2013.01)

(58) Field of Classification Search
CPC .... A61F 2002/91575; A61F 2002/9665; A61F 2250/0018; A61F 2/915; A61F 2/966
See application file for complete search history.

(56) References Cited

U.S. PATENT DOCUMENTS

| | | |
|---|---|---|
| 6,623,518 B2 | 9/2003 | Thompson et al. |
| 6,814,746 B2 | 11/2004 | Thompson et al. |
| 8,591,566 B2 | 11/2013 | Newell et al. |
| 8,696,729 B2 | 4/2014 | Thompson et al. |
| 9,044,351 B2 | 6/2015 | Wang et al. |
| 9,597,212 B2 | 3/2017 | Thompson et al. |
| 2002/0120323 A1 | 8/2002 | Thompson et al. |
| 2005/0222662 A1 | 10/2005 | Thompson et al. |
| 2009/0276027 A1 | 11/2009 | Glynn |

(Continued)

FOREIGN PATENT DOCUMENTS

| | | |
|---|---|---|
| CN | 101961269 A | 2/2011 |
| CN | 102065800 A | 5/2011 |

(Continued)

OTHER PUBLICATIONS

EP19162284.4, Extended European Search Report, dated Jul. 16, 2019, 7pgs.

(Continued)

*Primary Examiner* — Mohamed G Gabr
(74) *Attorney, Agent, or Firm* — Shumaker & Sieffert, P.A.

(57) ABSTRACT

In some examples, a catheter defines a longitudinal axis and includes an inner member, a retaining member, and a support member. The inner member has an outer wall, and a portion of the inner member has a first stiffness. The retaining member defines a pocket configured to receive a connecting member of an expandable medical device. The retaining member has a second stiffness that is different from the first stiffness. The support member extends distally from the retaining member. In some examples, the support member is configured to be received radially within the expandable medical device when the connecting member is received within the pocket. The support member is configured to provide a gradual transition between the first stiffness of the inner member and the second stiffness of the retaining member.

30 Claims, 22 Drawing Sheets

(56) References Cited

U.S. PATENT DOCUMENTS

| | | | |
|---|---|---|---|
| 2012/0078350 A1 | 3/2012 | Wang et al. | |
| 2013/0204344 A1 | 8/2013 | Tatalovich et al. | |
| 2013/0289698 A1* | 10/2013 | Wang .................... | A61F 2/2436 623/1.12 |
| 2015/0265443 A1 | 9/2015 | Wang et al. | |

FOREIGN PATENT DOCUMENTS

| | | |
|---|---|---|
| CN | 103126739 A | 6/2013 |
| CN | 104582643 A | 4/2015 |
| EP | 2623071 A1 | 7/2013 |
| WO | 20090134801 A2 | 11/2009 |
| WO | 2012036740 A2 | 3/2012 |

OTHER PUBLICATIONS

First Office Action and Search Report, and English translation thereof, from counterpart Chinese Aplication No. 201910188626.2, dated Nov. 30, 2020, 22 pp.

* cited by examiner

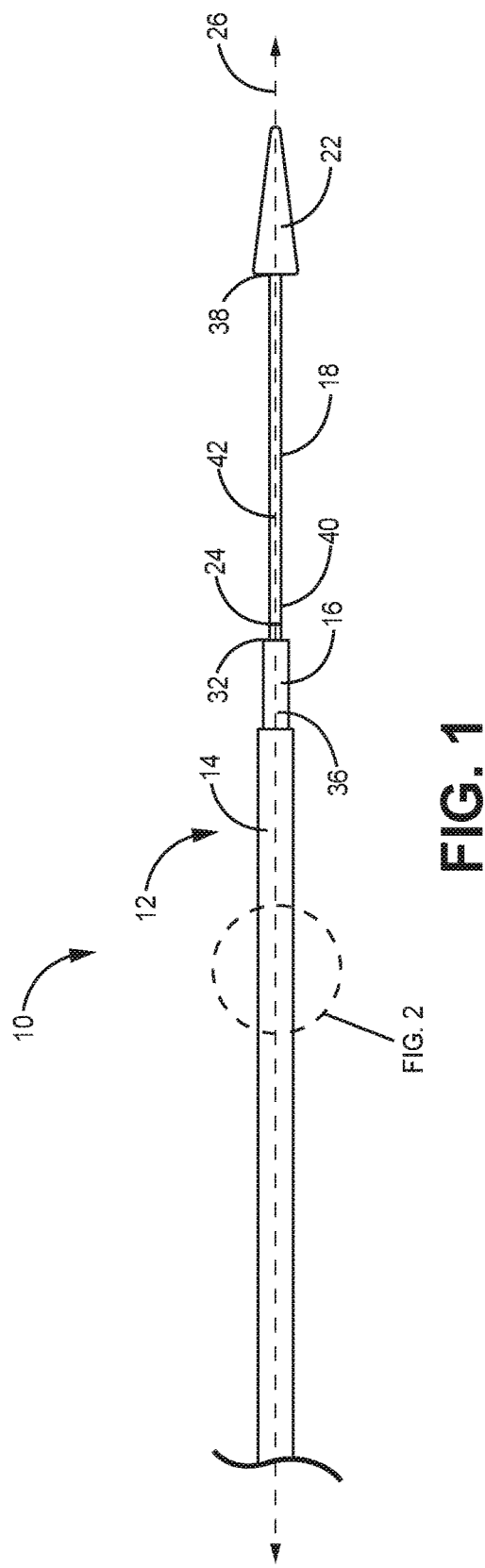
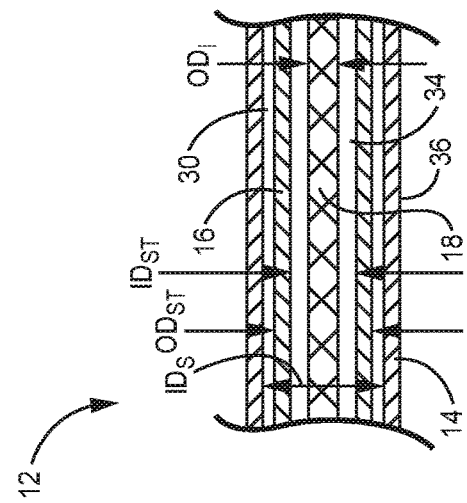
FIG. 1
FIG. 2

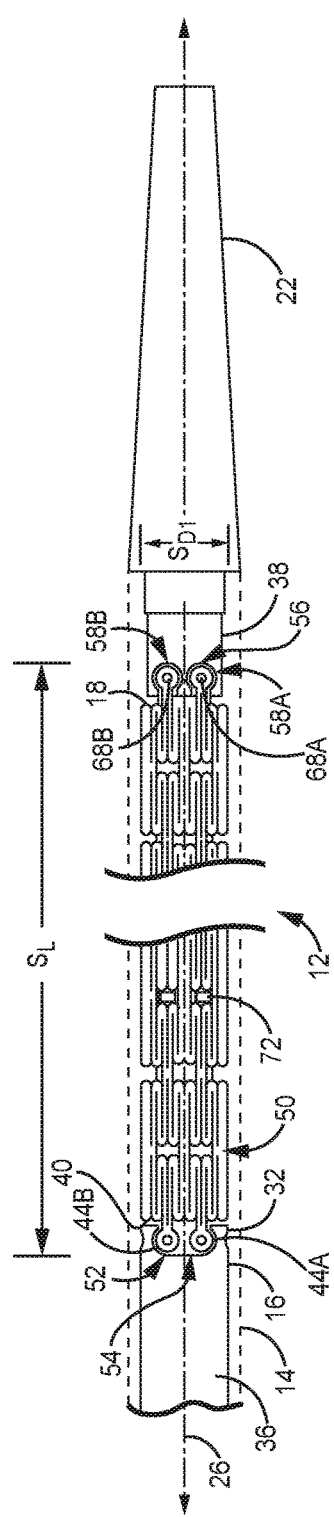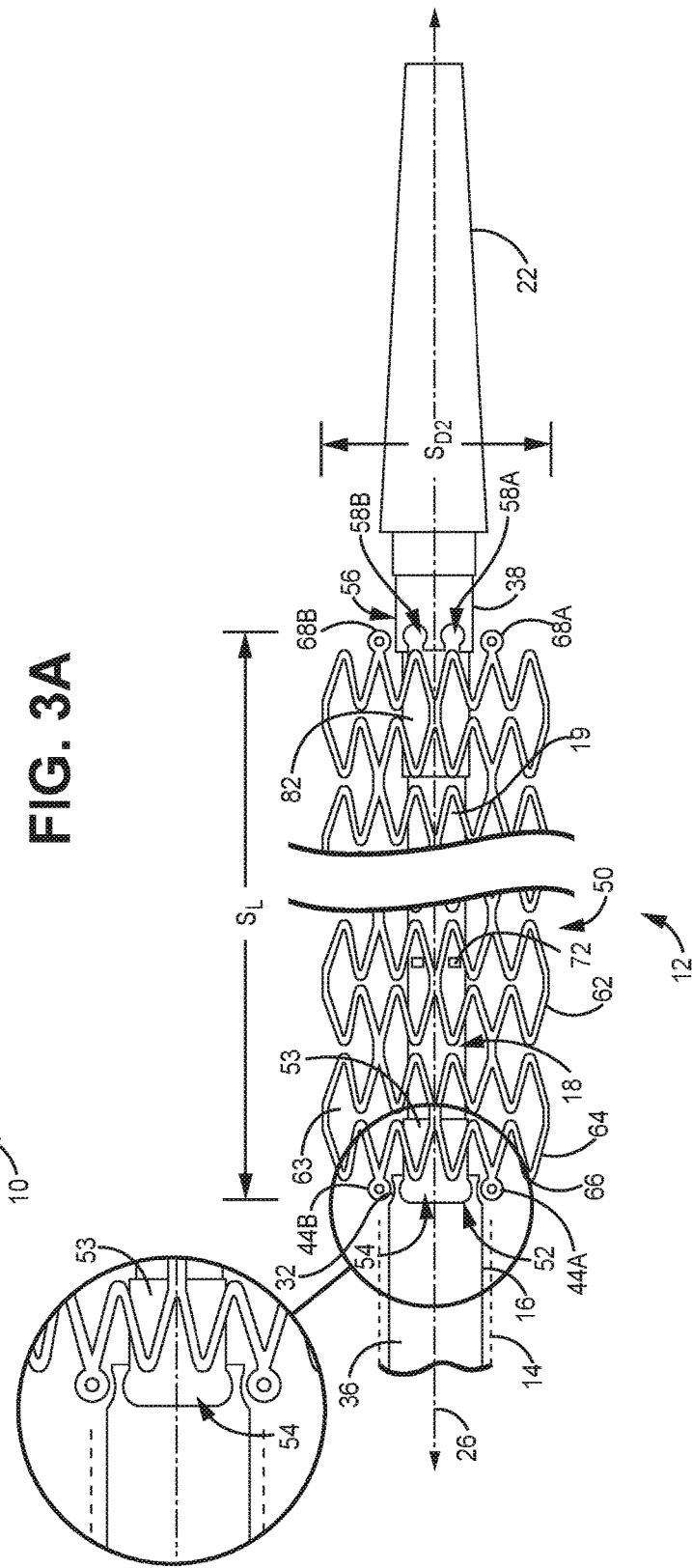
FIG. 3A
FIG. 3B

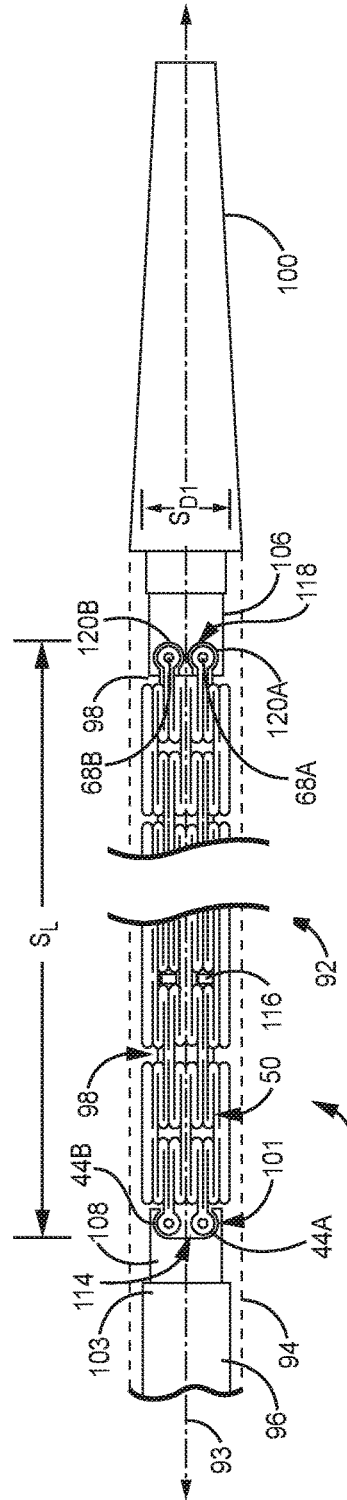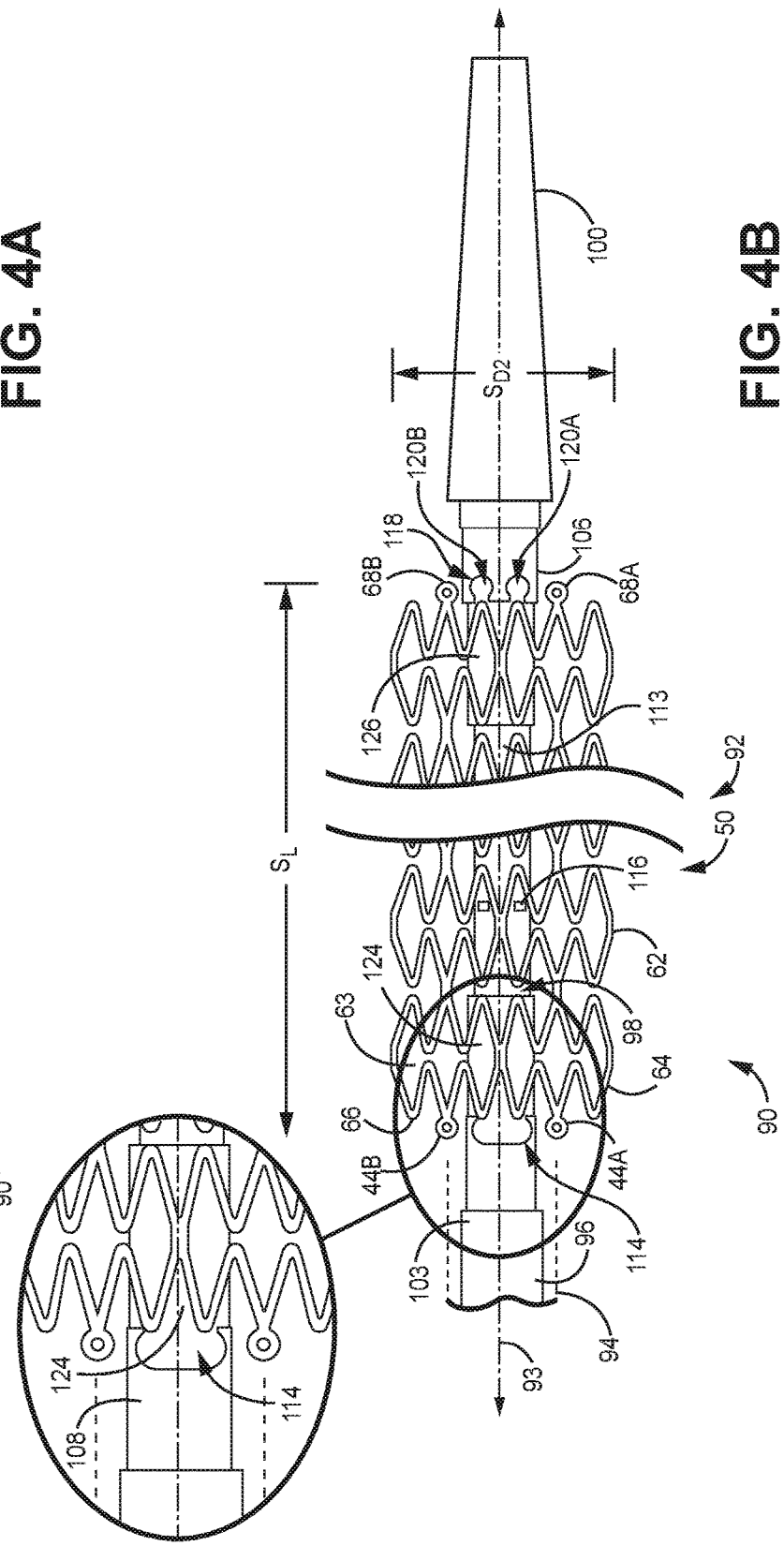

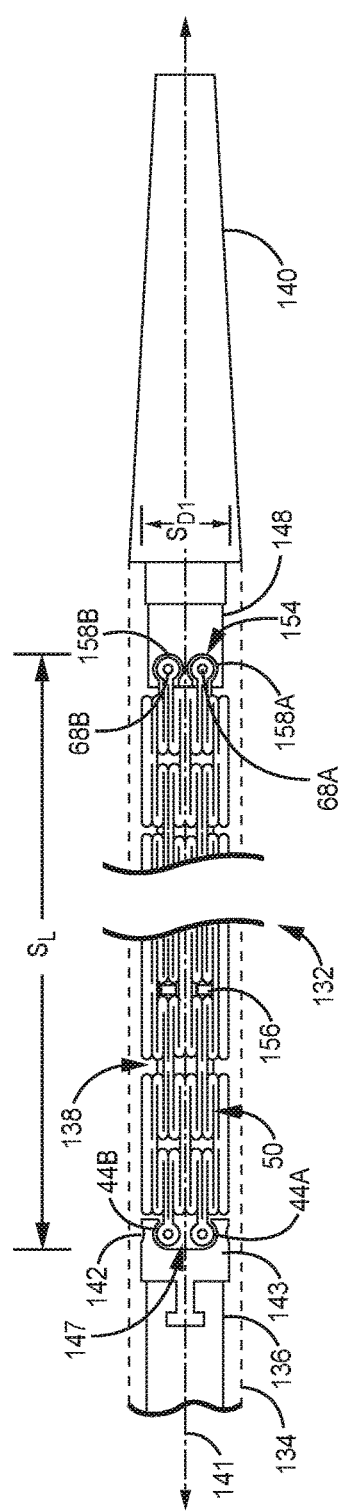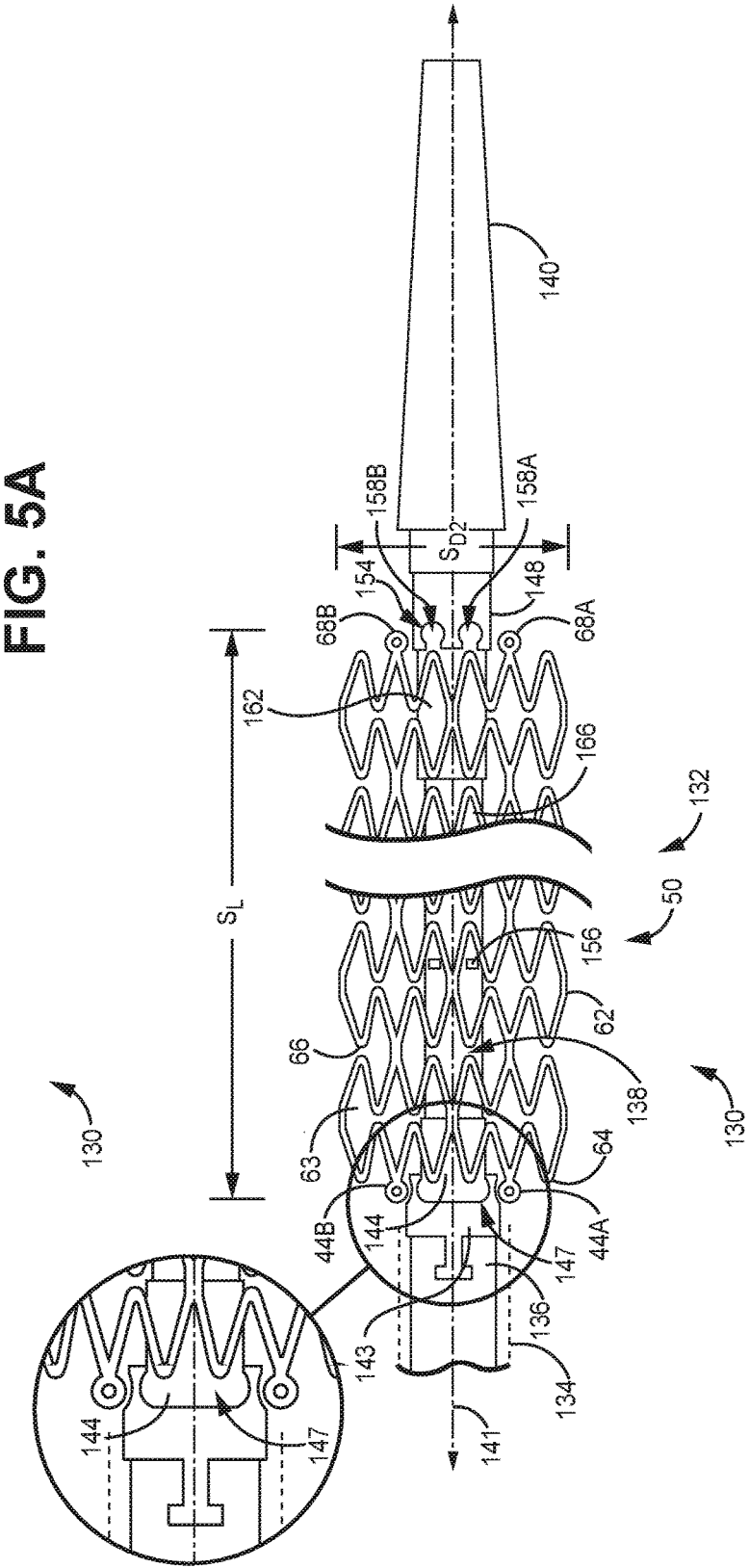

MEDICAL DEVICE DELIVERY SYSTEM INCLUDING A SUPPORT MEMBER

TECHNICAL FIELD

The disclosure relates generally to delivering a medical device to a treatment site within a patient.

BACKGROUND

Vessels may be treated to reduce or eliminate obstructions caused by atherosclerosis, arteriosclerosis, or other forms of vascular pathology. Interventional treatments can include the removal or widening of an obstruction by procedures such as angioplasty, which may include the inflation of a balloon to expand a narrowed lumen within an affected vessel. In some examples, vessels treated in this manner may become re-occluded due to the reformation of a plaque obstruction or due to weakening of the vessel wall.

To help maintain patency in vessels that have been treated to reduce or eliminate obstructions, stents and other expandable medical devices have been developed. During some medical procedures, an implant delivery system that includes a stent loaded onto a catheter and received within a sheath may be advanced to a treatment site within a vessel of a patient. Once the catheter has been advanced to a treatment site, withdrawal of the sheath from the catheter may allow the stent to self-expand and contact an inner surface of the wall of the vessel. Expandable stents can help maintain patency of a treated vessel by providing structural support to the vessel wall or by eluting substances that help reduce the proliferation of tissue on the inner surface of the vessel wall.

SUMMARY

This disclosure describes example medical device delivery systems, which can be used, for example, to deliver an expandable medical device (e.g., a stent or the like) during a medical procedure. In some examples, a medical device delivery system includes a catheter configured to retain an expandable medical device thereon while the catheter is navigated to a treatment site within the vasculature of a patient. The catheter includes an inner member, a retaining member configured to receive at least a portion of the expandable medical device, and a support member that extends from the retaining member and is configured to be received within the expandable medical device when the expandable medical device is received on the retaining member. The retaining member is configured to help retain the expandable medical device in place relative to the inner member, such as by limiting or even eliminating rotational movement of the medical device relative to the inner member. In some examples, the retaining member may be formed in a wall of the inner member or in a wall of a stop tube that is positioned over the inner member. In other examples, the catheter may include a retaining member that is separate from and mounted on the inner member or the stop tube, and configured to receive at least a portion of the expandable medical device. The support member may be configured to provide a gradual transition between the stiffness of the retaining member and the stiffness of the inner member or the stop tube.

Once the delivery system has been navigated to a treatment site within a target vessel, a sheath may be withdrawn from the catheter, thereby enabling the expandable medical device to expand outwardly from the catheter and into position against an inner surface of a wall of the target vessel. Also described herein are methods of using the catheter and related delivery systems.

Clause 1: In some examples, a catheter that defines a longitudinal axis comprises an inner member having an outer wall, wherein at least a portion of the inner member has a first stiffness; a retaining member defining a pocket configured to receive a connecting member of an expandable medical device, the retaining member having a second stiffness that is different from the first stiffness; and a support member extending distally from the retaining member, wherein the support member is configured to be received radially within the expandable medical device when the connecting member is received within the retaining member, and wherein the support member is configured to provide a gradual transition between the first stiffness of the inner member and the second stiffness of the retaining member.

Clause 2: In some of the examples of the catheter of clause 1, the retaining member is formed in the outer wall of the inner member, and the portion of the inner member having the first stiffness is distal to or proximal to the retaining member.

Clause 3: In some of the examples of the catheter of clause 2, the pocket extends through about 25% to about 75% of a thickness of the outer wall of the inner member.

Clause 4: In some of the examples of the catheter of any of clauses 1-3, at least a portion of the support member has a thickness that is less than the thickness of the outer wall of the inner member.

Clause 5: In some of the examples of the catheter of any of clauses 1-4, the retaining member defining a pocket is a proximal retaining member defining a proximal pocket and the connecting member is a proximal connecting member of the expandable medical device, the catheter further comprising a distal retaining member distal to the proximal retaining member, the distal retaining member defining a distal pocket being configured to receive a distal connecting member of the expandable medical device.

Clause 6: In some of the examples of the catheter of any of clauses 1-5, the support member is a proximal support member, the catheter further comprising a distal support member extending proximally from the distal retaining member.

Clause 7: In some of the examples of the catheter of any of clauses 1-6, the catheter further comprises a stop tube defining a lumen, wherein the inner member is received within the lumen of the stop tube.

Clause 8: In some of the examples of the catheter of clause 7, the retaining member is formed in the stop tube.

Clause 9: In some of the examples of the catheter of clause 7 or clause 8, the pocket extends through about 25% to about 75% of a thickness of an outer wall of the stop tube.

Clause 10: In some of the examples of the catheter of clause 9, at least a portion of the support member has a thickness that is less than the thickness of the outer wall of the stop tube.

Clause 11: In some of the examples of the catheter of any of clauses 7-10, the stop tube comprises a polymer material.

Clause 12: In some of the examples of the catheter of any of clauses 7-11 the stop tube comprises a metal.

Clause 13: In some of the examples of the catheter of any of clauses 7-12, at least one of the stop tube or the inner member comprises an echogenic or radiopaque material.

Clause 14: In some of the examples of the catheter of any of clauses 1-13, the support member extends distally of the retaining member and is radially offset from the pocket of the retaining member with respect to the longitudinal axis of the catheter.

Clause 15: In some of the examples of the catheter of any of clauses 1-14, the pocket defines at least one of a generally oval, circular, rectangular, or L-shape recessed region configured to receive the connecting member of the expandable medical device.

Clause 16: In some of the examples of the catheter of any of clauses 1-15, the support member comprises a tubular support member.

Clause 17: In some of the examples of the catheter of any of clauses 1-16, the retaining member defines a plurality of pockets, and each of the plurality of pockets is configured to receive a respective connecting member of a plurality of connecting members of the expandable medical device.

Clause 18: In some of the examples of the catheter of clause 17, the support member comprises a plurality of support members, and wherein a corresponding support member of the plurality of support members extends distally from each pocket of the plurality of pockets.

Clause 19: In some of the examples of the catheter of any of clauses 1-16, the retaining member defines only one pocket.

Clause 20: In some of the examples of the catheter of any of clauses 1-17, the catheter includes only one support member.

Clause 21: In some of the examples of the catheter of any of clauses 1-20, a surface of the support member defines at least one groove.

Clause 22: In some of the examples of the catheter of clause 21, the at least one groove includes a plurality of grooves, the grooves of the plurality of grooves being spaced along the surface of the support member in a direction orthogonal to the longitudinal axis of the catheter, and the grooves being spaced further apart at a distal end of the support member than at a proximal end of the support member.

Clause 23: In some of the examples of the catheter of clause 21, the at least one groove includes a plurality of grooves, the grooves of the plurality of grooves being spaced along the surface of the support member in a direction parallel to the longitudinal axis of the catheter.

Clause 24: In some examples, a delivery system comprises an expandable medical device having a proximal end and a distal end, the proximal end of the expandable medical device including at least one connecting member; a catheter defining a longitudinal axis, the catheter comprising: an inner member having an outer wall, wherein at least a portion of the inner member has a first stiffness; a retaining member defining a pocket configured to receive a connecting member of the expandable medical device, the retaining member having a second stiffness that is different from the first stiffness; and a support member extending distally from the retaining member, wherein the support member is configured to be received radially within the expandable medical device when the connecting member is received within the retaining member, and wherein the support member is configured to provide a gradual transition between the first stiffness of the inner member and the second stiffness of the retaining member; and a sheath mounted about the catheter and configured for longitudinal movement relative to the catheter.

Clause 25: In some of the examples of the delivery system of clause 24, the expandable medical device comprises a plurality of struts that form a plurality of cells.

Clause 26: In some of the examples of the delivery system of clause 25, the support member extends distally of a proximal-most row of cells of the plurality of cells when the connecting member is received within the pocket.

Clause 27: In some of the examples of the delivery system of clause 24, the expandable medical device comprises one or more compressible coils.

Clause 28: In some of the examples of the delivery system of any of clauses 24-27, the retaining member is formed in the outer wall of the inner member, and wherein the portion of the inner member having the first stiffness is distal to or proximal to the retaining member.

Clause 29: In some of the examples of the delivery system of clause 28, the pocket extends through about 25% to about 75% of a thickness of the outer wall of the inner member.

Clause 30: In some of the examples of the delivery system of clause 29, at least a portion of the support member has a thickness that is less than the thickness of the outer wall of the inner member.

Clause 31: In some of the examples of the delivery system of any of clauses 24-30, the retaining member defining a pocket is a proximal retaining member defining a proximal pocket and the connecting member is a proximal connecting member of the expandable medical device, the catheter further comprising a distal retaining member distal to the proximal retaining member, the distal retaining member defining a distal pocket being configured to receive a distal connecting member of the expandable medical device.

Clause 32: In some of the examples of the delivery system of clause 31, the support member is a proximal support member, the catheter further comprising a distal support member extending proximally from the distal retaining member.

Clause 33: In some of the examples of the delivery system of any of clauses 24-32, the catheter further comprises a stop tube defining a lumen, wherein the inner member is received within the lumen of the stop tube.

Clause 34: In some of the examples of the delivery system of clause 33, the retaining member is formed in the stop tube.

Clause 35: In some of the examples of the delivery system of clause 33 or clause 34, the pocket extends through about 25% to about 75% of a thickness of an outer wall of the stop tube.

Clause 36: In some of the examples of the system of clause 35, at least a portion of the support member has a thickness that is less than the thickness of the outer wall of the stop tube.

Clause 37: In some of the examples of the delivery system of any of clauses 33-36, the stop tube comprises a polymer material.

Clause 38: In some of the examples of the delivery system of any of clauses 33-37, the stop tube comprises a metal.

Clause 39: In some of the examples of the delivery system of any of clauses 33-38, at least one of the stop tube or the inner member comprises an echogenic or radiopaque material.

Clause 40: In some of the examples of the delivery system of any of clauses 24-39, the support member extends distally of the retaining member and is radially offset from the pocket of the retaining member with respect to the longitudinal axis of the catheter.

Clause 41: In some of the examples of the delivery system of any of clauses 24-40, the pocket defines at least one of a generally oval, circular, rectangular, or L-shape recessed region configured to receive the connecting member of the expandable medical device.

Clause 42: In some of the examples of the delivery system of any of clauses 24-41, the support member comprises a tubular support member.

Clause 43: In some of the examples of the delivery system of any of clauses 24-42, the retaining member defines a plurality of pockets, and each of the plurality of pockets is configured to receive a respective connecting member of a plurality of connecting members of the expandable medical device.

Clause 44: In some of the examples of the delivery system of clause 43, the support member comprises a plurality of support members, and wherein a corresponding support member of the plurality of support members extends distally from each pocket of the plurality of pockets.

Clause 45: In some of the examples of the delivery system of any of clauses 24-42, the retaining member defines only one pocket.

Clause 46: In some of the examples of the delivery system of any of clauses 24-43, the catheter includes only one support member.

Clause 47: In some of the examples of the system of any of clauses 24-46, a surface of the support member defines at least one groove.

Clause 48: In some of the examples of the delivery system of clause 47, the at least one groove includes a plurality of grooves, the grooves of the plurality of grooves being spaced along the surface of the support member in a direction orthogonal to the longitudinal axis of the catheter, and the grooves being spaced further apart at a distal end of the support member than at a proximal end of the support member.

Clause 49: In some of the examples of the delivery system of clause 47, the at least one groove includes a plurality of grooves, the grooves of the plurality of grooves being spaced along the surface of the support member in a direction parallel to the longitudinal axis of the catheter.

Clause 50: In some examples, a method comprises introducing a delivery system into a vessel of a patient, the delivery system comprising: an expandable medical device having a proximal end and a distal end, the proximal end of the expandable medical device including at least one connecting member; a catheter defining a longitudinal axis, the catheter comprising: an inner member having an outer wall, wherein at least a portion of the inner member has a first stiffness; a retaining member defining a pocket configured to receive a connecting member of the expandable medical device, the retaining member having a second stiffness that is different from the first stiffness; and a support member extending distally from the retaining member, wherein the support member is configured to be received radially within the expandable medical device when the connecting member is received within the retaining member, and wherein the support member is configured to provide a gradual transition between the first stiffness of the inner member and the second stiffness of the retaining member; and a sheath mounted about the catheter and adapted for longitudinal movement relative to the catheter; and withdrawing the sheath from the catheter to release the expandable medical device from the delivery system.

Clause 51: In some of the examples of the method of clause 50, the expandable medical device comprises a plurality of struts that form a plurality of cells.

Clause 52: In some of the examples of the method of clause 51, the support member extends distally of a proximal-most row of cells of the plurality of cells when the connecting member is received within the pocket.

Clause 53: In some of the examples of the method of clause 50, the expandable medical device comprises one or more compressible coils.

Clause 54: In some of the examples of the method of any of clauses 50-52, the retaining member is formed in the outer wall of the inner member, and wherein the portion of the inner member having the first stiffness is distal to or proximal to the retaining member.

Clause 55: In some of the examples of the method of clause 54, the pocket extends through about 25% to about 75% of a thickness of the outer wall of the inner member.

Clause 56: In some of the examples of the method of clause 55, at least a portion of the support member has a thickness that is less than the thickness of the outer wall of the inner member.

Clause 57: In some of the examples of the method of any of clauses 50-56, the retaining member defining a pocket is a proximal retaining member defining a proximal pocket and the connecting member is a proximal connecting member of the expandable medical device, the catheter further comprising a distal retaining member distal to the proximal retaining member, the distal retaining member defining a distal pocket being configured to receive a distal connecting member of the expandable medical device.

Clause 58: In some of the examples of the method of clause 57, the support member is a proximal support member, the catheter further comprising a distal support member extending proximally from the distal retaining member.

Clause 59: In some of the examples of the method of any of clauses 50-58, the catheter further comprises a stop tube defining a lumen, wherein the inner member is received within the lumen of the stop tube.

Clause 60: In some of the examples of the method of clause 59, the retaining member is formed in the stop tube.

Clause 61: In some of the examples of the method of clause 59 or clause 60, the pocket extends through about 25% to about 75% of a thickness of an outer wall of the stop tube.

Clause 62: In some of the examples of the method of clause 61, at least a portion of the support member has a thickness that is less than the thickness of the outer wall of the stop tube.

Clause 63: In some of the examples of the method of any of clauses 59-62, the stop tube comprises a polymer material.

Clause 64: In some of the examples of the method of any of clauses 59-63, the stop tube comprises a metal.

Clause 65: In some of the examples of the method of any of clauses 59-64, at least one of the stop tube or the inner member comprises an echogenic or radiopaque material.

Clause 66: In some of the examples of the method of any of clauses 50-65, the support member extends distally of the retaining member and is radially offset from the pocket of the retaining member with respect to the longitudinal axis of the catheter.

Clause 67: In some of the examples of the method of any of clauses 50-66, the pocket defines at least one of a generally oval, circular, rectangular, or L-shape recessed region configured to receive the connecting member of the expandable medical device.

Clause 68: In some of the examples of the method of any of clauses 50-67, the support member comprises a tubular support member.

Clause 69: In some of the examples of the method of any of clauses 50-68, the retaining member defines a plurality of pockets, and each of the plurality of pockets is configured to receive a respective connecting member of a plurality of connecting members of the expandable medical device.

Clause 70: In some of the examples of the method of clause 69, the support member comprises a plurality of support members, and wherein a corresponding support member of the plurality of support members extends distally from each pocket of the plurality of pockets.

Clause 71: In some of the examples of the method of any of clauses 50-68, the retaining member defines only one pocket.

Clause 72: In some of the examples of the method of any of clauses 50-69, the catheter includes only one support member.

Clause 73: In some of the examples of the method of any of clauses 50-72, a surface of the support member defines at least one groove.

Clause 74: In some of the examples of the method of clause 73, the at least one groove includes a plurality of grooves, the grooves of the plurality of grooves being spaced along the surface of the support member in a direction orthogonal to the longitudinal axis of the catheter, and the grooves being spaced further apart at a distal end of the support member than at a proximal end of the support member.

Clause 75: In some of the examples of the method of clause 73, the at least one groove includes a plurality of grooves, the grooves of the plurality of grooves being spaced along the surface of the support member in a direction parallel to the longitudinal axis of the catheter.

The details of one or more examples are set forth in the accompanying drawings and the description below. Other features, objects, and advantages of examples according to this disclosure will be apparent from the description and drawings, and from the claims.

BRIEF DESCRIPTION OF DRAWINGS

FIG. 1 is a side view of an example delivery system that includes a catheter configured for use in a medical procedure to introduce and deploy an expandable medical device (e.g., a stent) into a vessel within a body of a patient.

FIG. 2 is a is a partial cross-sectional view of a portion of the catheter of the delivery system of FIG. 1, and illustrates components of the delivery system of FIG. 1 in an assembled configuration.

FIG. 3A is a side view of a distal portion of the delivery system of FIG. 1, and illustrates connecting members of an expandable medical device received within a retaining member formed in a stop tube.

FIG. 3B is a side view of the distal portion of the delivery system of FIG. 3A, where the expandable medical device is shown expanding radially outwardly from the retaining member, e.g., during deployment of the stent from the delivery system, and illustrates that the stop tube further includes a support member received within stent.

FIG. 4A is a side view of another example delivery system and illustrates a connecting member of a stent received within a retaining member formed in an inner member of the delivery system.

FIG. 4B is a side view of the delivery system of FIG. 4A, where the stent is shown expanding radially outwardly from the retaining member in the inner member, e.g., during deployment of the stent from the delivery system, and illustrates that the inner member further includes a support member received within stent.

FIG. 5A is a side view of another example delivery system and illustrates connecting members of a stent received within a retaining member mechanically connected to a stop tube of the delivery system.

FIG. 5B is a side view of the delivery system of FIG. 5A, where the stent is shown expanding radially outwardly from the retaining member, e.g., during deployment of the stent from the delivery system, and illustrates that the stop tube further includes a support member received within stent.

DETAILED DESCRIPTION

Figure 3C:
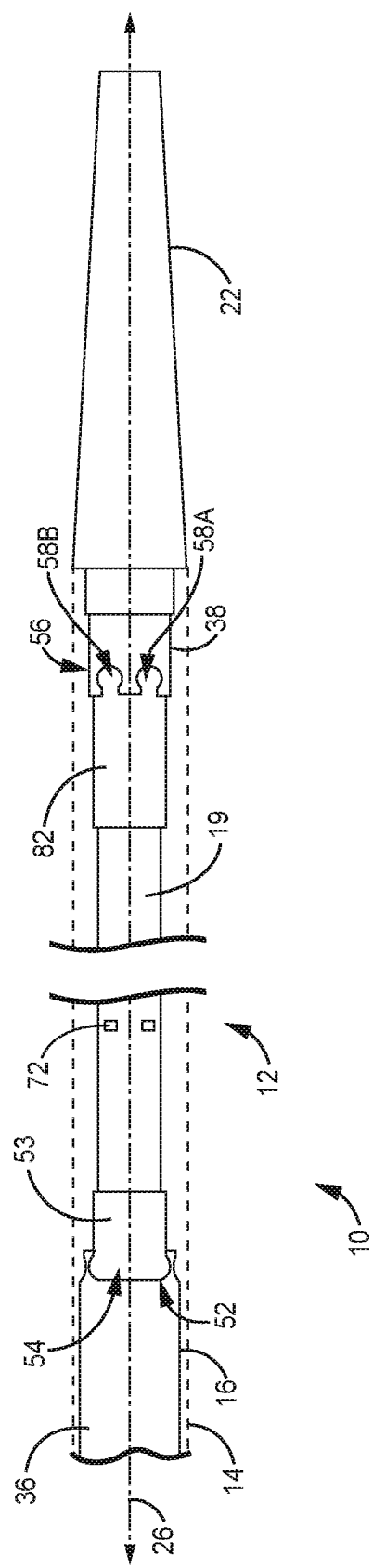
FIG. 3C is a side view of the distal portion of the delivery system of FIGS. 3A and 3B, where an expandable medical device is not received on the delivery system.

Healthy vessels within the human vasculature contain lumens sized to provide adequate transport of blood to and from the various tissues of the human body. Various pathologies of the vasculature can cause the stenosis, or narrowing, of a lumen of a blood vessel. For example, atherosclerosis occurs when a wall of an artery becomes thickened due to an accumulation of cholesterol-based plaque, cellular debris, and/or an abnormal growth of the cells of the arterial wall. The resultant restriction in blood flow through the narrowed lumen of the affected artery can lead to ischemia of the tissues fed by the artery. Options for restoring blood flow in vessels affected by conditions such as atherosclerosis include the removal of occlusive material from the lumen of the vessel, and the use of inflatable balloons (e.g., balloon angioplasty) to compress occlusive material and expand the lumen.

In addition to balloon angioplasty procedures that may improve blood flow through a treated vessel, a treated vessel may derive added clinical benefit from the placement of a structural support to help prevent re-narrowing of the treated vessel. Thus, some medical procedures may include placing an expandable medical device within a vessel of a patient to provide structural support to the vessel wall and help maintain patency of the vessel lumen. An example expandable medical device is a stent, which may include a tubular structure configured to expand with the aid of a balloon or configured to self-expand from a compressed configuration into an expanded configuration in which the stent contacts an inner surface of the vessel wall. When deployed in the expanded configuration within the target vessel, a stent may exert an outwardly-directed force that may help maintain the stent in place and provide long-term support to the target vessel. In some examples, a stent may be coated with a pharmacologically-active agent, such as an anticoagulant, anti-inflammatory agent, antiproliferative, or other drug, which may further help maintain the patency of the lumen of the target vessel.

While the disclosure primarily refers to stents, the expandable medical devices described herein can include other expandable medical devices, including, but not limited to, valves, stent-grafts, and the like. Further, the expandable medical devices may be self-expandable (e.g., formed from nitinol or another shape memory material), or may be balloon expandable.

In some examples, procedures for deploying a stent or other expandable medical device within a target vessel may include advancing a medical device delivery system, which may include a stent received on an inner member of a catheter and covered by a sheath, through the vasculature of a patient to a treatment site within a target vessel, and, in the case of a self-expandable stent, retracting the sheath to allow the stent to expand outwardly. In some examples, a stent may be maintained in the collapsed configuration under a biasing force, which may be supplied by an inner surface of a wall of the sheath. When the sheath is retracted, thereby removing the biasing force applied by the sheath, the stent may self-expand outwardly off from the catheter and into contact with the inner surface of the wall of the affected vessel.

In some examples, a catheter may include a retaining member or other feature that may be configured to receive a portion of the stent, referred to herein as a connecting member of the stent. The connecting member may, for example, be positioned at an end of the stent or near an end of the stent (e.g., closer to the end of the stent than a longitudinal center of the stent). An interlocking relationship between the connecting member of the stent and the retaining member of the catheter when the stent is received on the catheter may help retain the stent in place relative to the catheter during delivery of the stent to a treatment site within a vessel until the sheath has been sufficiently retracted from the stent. For example, the interlocking relationship between the connecting member of the stent and the retaining member of the catheter may help minimize or even prevent rotation of the stent relative to an inner member of the catheter. In some examples, the interlocking relationship between the connecting member and the retaining member may also help minimize or even prevent relative longitudinal movement (e.g., in a direction along a longitudinal axis of the catheter) of the stent relative to the inner member of the catheter. For example, the retaining member may help prevent the stent from jumping distally out from the sheath during retraction of the sheath from the inner member. By helping to retain the stent in place relative to the catheter, the retaining member may enable more predictable deployment of the stent at the treatment site within the target vessel.

A retaining member of the catheter may be formed by any suitable part of the catheter. For example, the retaining member may be formed within a wall of a component of the catheter, such as an inner member or a stop tube. In some examples, instead of being referred to as a "retaining member," a feature configured to receive a portion of a stent interchangeably may be referred to as an "interlock structure." In some examples, the catheter may include a retaining member that is separate from the inner member or stop tube and configured to receive a portion of a stent (e.g., a connecting member of the stent). In such examples, the retaining member may be configured to fit over an outer dimension of a portion of the catheter (e.g., a stop tube or an inner member), and may be bonded, crimped, swaged, welded to, or otherwise secured to the stop tube or inner member of the catheter. An interlocking relationship between the connecting member of the stent and the retaining member of the catheter when the stent is received on the catheter may help retain the stent in place relative to the catheter during delivery of the stent to a treatment site within a vessel until the sheath has been sufficiently retracted from the stent. For example, the interlocking relationship between the connecting member of the stent and the retaining member of the catheter may help minimize or even prevent rotation of the stent relative to an inner member of the catheter.

In examples in which the retaining member is separate from the stop tube or the inner member, the retaining member may be formed from a polymer or from a metal. However, in some cases, a metal retaining member may not be configured to flex as much as a polymer retaining member when a delivery system that includes the retaining member is advanced through tortuous vasculature of a patient, which may result in undesirable kinking or bending of the delivery system. Thus, in examples in which a catheter includes a retaining member that is formed separately from an inner member or a stop tube of a catheter instead of a retaining member that is formed by an inner member or stop tube, it may be desirable to form the retaining member from a polymer.

Retaining members that are formed separately from an inner member or a stop tube of a catheter may require manufacturing resources (e.g., molds and assembly time) in addition to those needed to manufacture and assemble the stop tube and inner member. Thus, in some examples, it may be less expensive and/or less time consuming to include a retaining member that is formed integrally with a portion of a catheter (e.g., integrally formed with a stop tube or an inner member). In such examples, the inner member and the stop tube may be formed from a polymer, and the retaining member may include one or more recessed regions (e.g., "pockets," as described below) of the polymer material of the inner member or stop tube.

A portion of a catheter that includes the retaining member may have a stiffness that is different from a stiffness of a portion of the catheter that is distal to the retaining member. The difference in stiffness may be at least partially attributable to a difference in wall thickness of these portions of the catheter; the bend strength of the catheter may vary with the wall thickness. The wall thickness may be, for example, the dimension of the catheter that occupies the space between an inner lumen of the catheter and an outer surface of the catheter, as measured in a direction orthogonal to the longitudinal axis of the catheter. For example, the portion of the catheter that includes the retaining member may have a thicker wall than the portion of the catheter distal to the retaining member. The portion of the catheter distal to the retaining member may, for example, only include the inner member whereas the portion of the catheter including the retaining member may include both the inner member and another structure, such as a stop tube or a retaining structure separate from a stop tube and the inner member. As another example, if the inner member defines the retaining member, the wall thickness of the inner member at the portion of the catheter distal to the retaining member may be narrower than the portion of the inner member defining the retaining member.

In examples in which a portion of a catheter that includes retaining member that has a stiffness that is different from a stiffness of a portion of the catheter that is distal to the retaining member, the catheter may be prone to kinking at the junction of the portion of the catheter that includes the retaining member and the portion of the catheter that is distal to (or, in some examples, proximal to) the retaining member due to a relatively abrupt change in stiffness of the catheter at the junction. This junction may be referred to as a kink point. In some examples, when a stent is received within the retaining member, the stent may extend from the retaining member over the kink point. In some examples, a kink point between different portions of a catheter may cause undesirable bending (or kinking) of the catheter and/or of the stent while the delivery system is being advanced through the vasculature of a patient to the treatment site, which may reduce the ease with which a clinician may navigate the catheter through the vasculature and complicate efforts to advance the catheter through the vasculature of a patient to the treatment site.

In examples described herein, a catheter may include a support member that is configured to provide a gradual stiffness transition between a component of the catheter having a relatively greater stiffness, such as a portion of the catheter that includes a retaining member, and a portion of the catheter that is relatively less stiff, such as a portion of the catheter that extends proximally or distally beyond the retaining member. The support member may provide a more gradual stiffness change between the retaining member and a less stiff portion of the catheter distal to or proximal to the retaining member relative to examples in which the catheter does not include the support member. In some examples, a support member may extend proximally or distally from an end of the retaining member, and may be configured to be received radially within the stent when a connecting member of the stent is received within the retaining member of the catheter. The gradual transition in stiffness between portions of the catheter provided by the support member may reduce or eliminate the possibility that the catheter will kink at the end of the retaining member during navigation of the catheter through vasculature of the patient. In this way, the support member may provide stability to the catheter, which may help increase the navigability of the catheter and improve the ease with which the catheter may be advanced through the vasculature of a patient.

In some examples, the support member may also be configured to help reduce the stress on a stent as the stent is being deployed from the delivery device. As a clinician begins to retract a sheath relative to a stent positioned on a catheter, a distal portion of the stent may be exposed and begin to expand while a proximal portion of the stent is still positioned on the catheter and received within the sheath. In examples in which a catheter does not include a support member, the expansion of the distal portion of the stent may cause the stent to laterally bend or flex. This may occur in instances in which the inner surface of the wall of the target vessel into which the stent is being deployed has an uneven or irregular surface, which may be caused by uneven compression of occlusive material during balloon angioplasty, a natural curvature or narrowing of the vessel, or other causes. When the stent is still mounted around the support member, the support member may provide structural support to the stent from the inner surface of the stent, which may help reduce the bend radius of the stent as it is being deployed from the delivery device.

A portion of the retaining member that is configured to receive one or more of the connecting members of the stent in an interlocking relationship may be referred to as a "pocket." As described above, the retaining member may be formed within a wall of a component of the catheter, such as an inner member or a stop tube. In other examples, a catheter may include a retaining member that is separate from and attached to the inner member or the stop tube. In examples in which the catheter includes a retaining member that is formed in a wall of a component of the catheter, e.g., a stop tube, the pocket may be a recessed region having a perimeter defined by an outer surface of the wall of the stop tube and extending partially through a thickness of the wall to a depth suitable for securely receiving a connecting member. Because the pocket extends only partially through the thickness of the wall, the pocket includes a floor formed by the material of the wall, upon which the connecting member may be supported when the connecting member is received within the pocket.

In contrast, in a retaining member that defines through-holes that extend through an entire thickness of a wall of a portion of the catheter (e.g., a stop tube), the through-holes may weaken the portion of the catheter in which the through-holes are formed, leading to uneven distribution of torque forces and possible reduction in structural stability of an expandable medical device (e.g., a stent) retained on the catheter. In addition, when a connecting member of a stent is received within a retaining member of a catheter that defines through-holes, the connecting member may be capable of a greater range of motion relative to a connecting member received within a retaining member that defines a pocket. A relatively greater range of motion of the connecting member within the through-hole may in turn cause undesirable rotation of the stent relative to the catheter. A pocket, however, may be formed to a depth that corresponds to a thickness of the connecting members of a stent. For example, pockets configured to accommodate a thin connecting member may have a relatively shallow depth compared to pockets that are configured to accommodate thicker connecting members. Thus, the floor of a pocket may help limit movement of the connecting member within the pocket, thereby providing the stop tube with structural integrity and resistance to undesirable movement. In examples in which a retaining member is integrally formed with a portion the catheter (e.g., a stop tube or an inner member), the retaining member may be formed in any suitable manner, such as by laser cutting, machining, or molding the pockets in the portion of the catheter.

While the present disclosure describes devices and systems including catheters and implant delivery systems primarily in the context of stent-delivery procedures for treating atherosclerosis, the devices and systems of the present disclosure may also be used to deliver stents configured to provide mechanical support to other lumens within the body of a patient, such as a lumen of a fallopian tube, urethra, esophagus, bile duct, pancreas, colon, or other anatomical structure. Further, the catheters described herein may be used with various types of stents and stent delivery systems.

FIG. 1 is a side view of an example delivery system 10 that includes a catheter 12 configured for use in a medical procedure to introduce and deploy an expandable medical device (e.g., a stent), into a vessel within a body of a patient. FIG. 2 is a partial cross-sectional view of a portion of catheter 12 of delivery system 10 of FIG. 1, and illustrates components of delivery system 10 in an assembled configuration. Catheter 12 includes a sheath 14, a stop tube 16, an inner member 18, a distal tip 22, and a marker 24. Catheter 12 may define a longitudinal axis 26, which may be a central longitudinal axis of one or more of the components of catheter 12, such as sheath 14, stop tube 16, and inner member 18.

Sheath 14 defines a lumen 30 (shown in FIG. 2) configured to receive inner member 18 and stop tube 16. In FIG. 1, sheath 14 is illustrated as being at least partially retracted, thus exposing portions of stop tube 16 and inner member 18. Stop tube 16 includes a distal portion 32, defines a lumen 34 (shown in FIG. 2) configured to receive inner member 18, and includes an outer wall 36. Inner member 18 includes a distal portion 38, and a proximal portion 40. In some examples, inner member 18 may define a lumen which may be configured to receive a guidewire (not shown) over which delivery system 10 may be advanced. As described below with respect to FIGS. 4A and 4B, either or both of stop tube 16 and inner member 18 may be configured to retain an expandable medical device thereon.

Distal tip 22 extends distally of distal portion 38 of inner member 18. In some examples, distal tip 22 may be a separate component connected to inner member 18, such as by adhesives or an interference fit between the two components. In other examples, distal tip 22 may be integrally formed with the inner member 18. When delivery system 10 is in the assembled configuration, the narrow profile of the distal tip 22 positioned at distal portion 38 of inner member 18 may facilitate advancement of the catheter 12 of the delivery system 10 through the vasculature of a patient.

In some examples, stop tube 16 may have a rigidity that is greater than a rigidity of inner member 18. The greater rigidity of stop tube 16 relative to inner member 18 may be provided by a material of stop tube 16 that is more rigid than a material of the inner member 18. Additionally, or alternatively, outer wall 36 of stop tube 16 may have a thickness that is greater than a thickness of an outer wall of inner member 18. In any such examples, stop tube 16 may provide additional column strength to catheter 12 of delivery system 10, such that pushability of catheter 12 through the vasculature of a patient is improved relative to example delivery systems not including stop tube 16. Marker 24 may be a marker configured to enable a clinician to visualize a junction between stop tube 16 and inner member 18 during a medical procedure. For example, marker 24 may include a radiopaque, echogenic, or other type of material suitable for imaging during a medical procedure.

As shown in FIG. 2, sheath 14 may have an inner dimension (e.g., an inner diameter) $ID_S$ such that lumen 30 of sheath 14 has a diameter of $ID_S$. Stop tube 16 may have an outer dimension (e.g., an outer diameter) $OD_{ST}$ and an inner dimension $ID_{ST}$, such that lumen 34 of stop tube 16 has a diameter of $ID_{ST}$. Diameter $OD_{ST}$ may be sufficiently less than inner dimension $ID_S$ of sheath 14 to enable stop tube 16 to be received within lumen 30 of sheath 14. Inner member 18 may have an outer dimension $OD_I$, which may be sufficiently less than $ID_{ST}$ of stop tube 16 to enable inner member 18 to be received within lumen 34 of stop tube 16. When delivery system 10 is in the assembled configuration shown in FIG. 1, proximal portion 40 of inner member 18 is at least partially received within lumen 34 of stop tube 16. When sheath 14 is distally extended, both inner member 18 and stop tube 16 may be received within lumen 30 of sheath 14. Although $ID_S$ and $ID_{ST}$ are depicted in the illustrated example of FIG. 2 as being significantly larger than respective ones of $OD_{ST}$ and $OD_I$, in other examples, the components of catheter 12 may fit together more snugly, e.g., without significant gaps between stop tube 16 and lumen 30 of sheath 14, or between inner member 18 and lumen 34 of stop tube 16. With the components of catheter 12 of delivery system 10 so assembled, sheath 14 may be movable in a direction parallel to longitudinal axis 26, such that sheath 14 may be distally advanced or proximally retracted with respect to inner member 18.

FIGS. 3A and 3B illustrate a distal portion of delivery system 10 of FIG. 1. FIG. 3A is a side view of a distal portion of delivery system 10 of FIG. 1, and illustrates connecting members 44A and 44B of an expandable medical device 50 received within a retaining member 52 formed in stop tube 16. FIG. 3B is a side view of the distal portion of delivery system 10, where expandable medical device 50 (which may be referred to herein as a stent) is shown expanded radially outwardly from retaining member 52, e.g., after deployment of stent 50 from delivery system 10, and illustrates that stop tube 16 further includes a support member 53 received within stent 50. FIG. 3C is a side view of the distal portion of delivery system 10, where an expandable medical device is not received on delivery system 10.

As illustrated in FIG. 3A, stent 50 is configured to engage with retaining member 52, which comprises at least one pocket 54, which is defined by wall 36 of stop tube 16. When a portion of stent 50 is received in pocket 54 defined by retaining member 52, retaining member 52 may help limit or even prevent rotation of stent 50 relative to catheter 12. In the example shown in FIG. 3A, retaining member 52 is formed in stop tube 16 in distal portion 32 of stop tube 16. In other examples, e.g., as described with respect to FIGS. 4A-5B, retaining member 52 may be formed in another structure of system 10, such as, but not limited to, inner member 18 or an interlocking structure separate from inner member 18 and stop tube 16.

In the example shown in FIG. 3A, a proximal end of stent 50 is engaged with retaining member 52. In some examples, a distal end of stent 50 may also be engaged with a respective retaining member. For example, retaining member 52 may be a proximal retaining member and distal portion 38 of inner member 18 may include a distal retaining member 56. Although the example of system 10 shown in FIGS. 3A-3C includes both retaining member 52 and distal retaining member 56, other examples of system 10 may include one of retaining member 52 or distal retaining member 56. Like retaining member 52, distal retaining member 56 may define one or more pockets configured to receive a portion of stent 50. For example, in the example shown in FIGS. 3A-3C, distal retaining member 56 defines a first distal pocket 58A and a second distal pocket 58B. In some examples, at distal retaining member 56, distal portion 38 of inner member 18 may have an outer dimension (e.g., an outer diameter) that is substantially the same as an outer dimension (e.g., an outer diameter) of stop tube 16 at proximal retaining member 52. In addition, distal portion 38 of inner member 18 may have an outer dimension greater than an outer dimension (e.g., a diameter) of intermediate portion 19 of inner member 18 that is proximal to distal portion 38 and distal to proximal portion 40. In some examples, the enlarged outer dimension of distal portion 38 of inner member 18 may provide structural support to distal portion 38 of inner member 18 when stent 50 is received on the delivery system 10.

In some examples, proximal retaining member 52 and distal retaining member 56 may have substantially similar dimensions; e.g., similar diameters and/or similar lengths. In other examples, the dimensions of proximal retaining member 52 and distal retaining member 56 may differ. For example, a diameter of proximal retaining member 52 may be greater than a diameter of distal retaining member 56. However, in such examples, pocket 54 of proximal retaining member 52 and distal pockets 58A, 58B may be formed in respective ones of stop tube 16 and inner member 18 such that each of connecting members 44A, 44B, 68A, and 68B are substantially equidistant from longitudinal axis 26 when connecting members 44A, 44B, 68A, and 68B are retained within respective ones of pocket 54 and distal pockets 58A, 58B. For example, the floor of each of pockets 54, 58A, and 58B may be equidistant from longitudinal axis 26. Thus, even in examples in which the dimensions of proximal retaining member 52 and distal retaining member 56 differ, stent 50 may be retained on catheter 12 in such a manner that stent diameter SD is substantially the same at connecting members 44A, 44B as at connecting members 68A, 68B, which may provide stability to catheter 12 of delivery system 10, thereby improving the ease with which delivery system 10 may be advanced through the vasculature of a patient.

Sheath 14 is configured to extend over stent 50 to retain stent 50 in a compressed configuration, as shown in FIG. 3A. In the example of FIGS. 3A-3C, the stent 50 includes a first distal connecting member 68A and a second distal connecting member 68B, as well as a first proximal connecting member 44A and a second proximal connecting member 44B. Stent 50 has a stent length "$S_L$" (measured parallel to longitudinal axis 26 when stent 50 is received on catheter 12 of delivery system 10) and a compressed stent diameter "$S_{D1}$" measured orthogonal to the longitudinal axis 26 when stent 50 is received on catheter 12 of stent delivery system 10. Although $S_{D1}$ is described herein as being a diameter of stent 50, in some examples, stent 50 may have a non-circular cross-sectional shape in other examples, such that $S_{D1}$ may be any greatest dimension of stent 50 measured orthogonal to longitudinal axis 26 when stent 50 is in the compressed configuration. Stent 50 further includes a plurality of struts 62. The struts 62 may define any suitable pattern and cell structure (e.g., open cells or closed cells), including a first row of cells 63. For example, struts 62 may define a serpentine, zig-zag, or accordion-like pattern. In other examples, struts 62 of stent 50 may have other configurations, such as one or more compressible coils.

Distal connecting members 68A, 68B are configured to be received in distal pockets 58A, 58B of distal retaining member 56, and proximal connecting members 44A, 44B are configured to be received within proximal retaining member 52 formed in stop tube 16. When connecting members 44A, 44B, 68A, and 68B of stent 50 are received within respective ones of pockets 58A, 58B, and 54 of proximal retaining member 52 and distal retaining member 56, the interlocking relationship between respective ones of connecting members 44A, 44B, 68A, and 68B and retaining members 52 and 56 may help retain stent 50 in a desired position relative to inner member 18 as catheter 12 is advanced to a treatment site within the vasculature of a patient, and may also help prevent the stent 50 from being released from catheter 12 until the sheath 14 has been retracted proximally past the proximal retaining member 52 of stop tube 16. For example, the interlocking relationship between respective ones of connecting members 44A, 44B, 68A, and 68B of stent 50 and retaining members 52, 56 may help minimize or even prevent rotation of stent 50 relative to stop tube 16. In some examples, the interlocking relationship between connecting members 44A, 44B of stent 50 and retaining member 52 of stop tube 16 may also help minimize or even prevent longitudinal movement (e.g., in a direction along longitudinal axis 26) of stent 50 relative to stop tube 16. For example, pocket 54 of proximal retaining member 52 may help prevent stent 50 from moving longitudinally and distally relative to catheter 12 during retraction of sheath 14 (in a proximal direction) from stop tube 16. By helping to retain stent 50 in place relative to catheter 12, retaining members 52 and 56 of catheter 12 may enable more predictable deployment of stent 50 at a treatment site within the target vessel.

In the example of FIG. 3A, pocket 54 of proximal retaining member 52 of stop tube 16 is configured to receive both of proximal connecting members 44A, 44B. However, in other examples, proximal retaining member 52 may have different configurations. For example, proximal retaining member 52 may be configured to receive only one of proximal connecting members 44A, 44B. In such examples or in the example shown in FIG. 3A, proximal retaining member 52 of stop tube 16 may define one or more additional pockets, which are not visible in the side view of FIG. 3A, but which may be positioned at the distal portion 32 of stop tube 16 on the opposite side of longitudinal axis 26 from pocket 54 of the proximal retaining member 52.

As also shown in FIG. 3A, first distal pocket 58A is configured to receive first distal connecting member 68A, and second distal pocket 58B is configured to receive second distal connecting member 68B. In some examples, distal portion 38 of inner member 18 may include one or more additional pockets, which are not visible in the side view of FIG. 3A, but which may be formed in distal portion 38 of inner member 18 on the opposite side of longitudinal axis 26 from first distal pocket 58A and second distal pocket 58B. In other examples, as with proximal retaining member 52 illustrated in FIG. 3A, distal portion 38 of inner member 18 may include a single pocket configured to receive both of distal connecting members 68A, 68B.

In the example of FIG. 3A, distal portion 38 of inner member 18 may have substantially the same outer dimension (e.g., outer diameter) as an outer dimension (e.g., outer diameter) of stop tube 16 at proximal retaining member 52. Thus, when the connecting members of stent 50 are received within the respective pockets 54, 58A, 58B of stop tube 16 and inner member 18 and stent 50 is housed within sheath 14, stent 50 may be evenly compressed along stent length $S_L$ such that stent diameter $S_{D1}$ is substantially the same along the entirety of stent length $S_L$. In other examples, inner member 18 may not include distal portion 38 or distal pockets 58A, 58B. Instead of, or in addition to, distal portion 38, inner member 18 may include one or more intermediate interlocks 72. Intermediate interlocks 72 may be one or more protrusions configured to fit between struts 62 of stent 50 when stent 50 is retained on catheter 12 of delivery system 10, thereby restraining stent 50 from rotational movement as sheath 14 is retracted. In some examples, intermediate interlocks 72 may be molded integrally with inner member 18. In other examples, intermediate interlocks 72 may be mechanically connected to inner member 18 by any suitable technique, such as by adhesives or welding.

The side view of FIG. 3B shows stent 50 in an expanded state, after stent 50 has radially expanded outwardly from the proximal retaining member 52 of stop tube 16 during deployment of stent 50 from catheter 12. Sheath 14 has been retracted proximally to a position proximal of the retaining member 52, enabling stent 50 to expand from the compressed configuration of FIG. 3A to the expanded configuration shown in FIG. 3B. As the stent expands from the compressed configuration of FIG. 3A to the expanded configuration of FIG. 3B, connecting members 68A, 68B, 44A, and 44B of stent 50 disengage from pockets 58A, 58B, and 54, and the spaces between struts 62 disengage from intermediate interlocks 72. Upon release of stent 50 from delivery system 10, stent 50 expands to an expanded configuration in which a diameter of stent 50 increases from compressed stent diameter "$S_{D1}$" to larger, expanded stent diameter "$S_{D2}$." In some examples, compressed stent diameter $S_{D1}$ may be from about 1.2 millimeters (mm) to about 4.4 mm, and may correspond to an inner diameter (e.g., diameter) of sheath 14, as self-expansion of stent 50 within lumen 30 of sheath 14 may bring stent 50 into contact with an inner surface of sheath 14 while stent 50 is received within lumen 30 (shown in FIG. 2).

When stent 50 is in the expanded configuration, expanded stent diameter $S_{D2}$ enables stent 50 to contact the inner surface of a wall of the target vessel in order to support patency of the lumen of the target vessel. The dimensions of the expanded configuration of stent 50 (e.g., $S_{D2}$ and $S_L$) may be selected based on an inner dimension (e.g., a circumference of a lumen) of the target vessel and a length of the treatment area within the target vessel. For example, the expanded stent diameter $S_{D2}$ may be from about 5 mm to about 25 mm, while the stent length $S_L$ may be from about 30 mm to about 200 mm. With stent 50 deployed in the expanded configuration at the treatment site within the target vessel, delivery system 10 then may be withdrawn proximally through the vasculature of the patient and removed from the patient's body.

Catheter 12 further includes support member 53, which extends from proximal retaining member 52 and is configured to provide a more gradual stiffness change between proximal retaining member 52 and a less stiff portion of the catheter 12 (e.g., a portion of inner member 18) distal to retaining member 52, relative to examples in which catheter 12 does not include support member 53. In some examples, support member 53 may extend distally from retaining member 52, such as from pocket 54, and may be configured to be received radially within stent 50 when one or both of proximal connecting members 44A, 44B of stent 50 are received within pocket 54 of retaining member 52. The gradual transition in stiffness between portions of catheter 12 provided by support member 53 may reduce or eliminate the possibility that catheter 12 will kink at an end of retaining member 52, such as at pocket 54 or at the junction of inner member 18 and distal portion 32 of stop tube 16. In this way, support member 53 may help increase the navigability of catheter 12, and improve the ease with which catheter 12 may be advanced through the vasculature of a patient.

In the example shown in FIG. 3B, support member 53 extends distally of distal portion 32 of the stop tube 16 and is formed integrally with stop tube 16. In some examples, support member 53 of FIG. 3B is a tubular extension of stop tube 16 that is configured to be received radially within stent 50. In some examples, support member 53 may extend distally within stent 50 past a first row of cells 63 of stent 50 when stent 50 is received on inner member 18 and stop tube 16. Support member 53 may have a thickness that is less than a thickness of a wall of stop tube 16. This difference in thickness of stop tube 16 and support member 53 may provide a gradual transition in stiffness between stop tube 16 (which may have a greater stiffness than inner member 18), and inner member 18. In some cases, this gradual transition in stiffness provided by support member 53 may be advantageous to the operation of delivery system 10. For example, the gradual transition in stiffness provided by support member 53 may help prevent a kink point from occurring at the junction of inner member 18 and distal end 32 of stop tube 16. In this way, support member 53 may provide stability to catheter 12 of delivery system 10, thereby improving the ease with which delivery system 10 may be advanced through the vasculature of a patient.

In addition, support member 53 may also be configured to help reduce the stress on stent 50 as stent 50 is being deployed from delivery system 10. As a clinician begins to proximally retract sheath 14 relative to stent 50 when stent 50 is positioned on catheter 12, a distal portion of stent 50 may be exposed and may therefore begin to expand while a proximal portion of stent 50 is still positioned on stop tube 16 and received within sheath 14. In examples in which stop tube 16 does not include support member 53, the expansion of the distal portion of stent 50 may cause stent 50 to laterally bend or flex. This may occur, for example, in instances in which the inner surface of the wall of the target vessel into which the stent is being deployed has an uneven or irregular surface, which may be caused by uneven compression of occlusive material during balloon angioplasty, a natural curvature or narrowing of the vessel, or in other instances. In examples in which stop tube 16 does include support member 53, when stent 50 is still mounted around support member 53, support member 53 may provide structural support to stent 50 from an inner surface of stent 50, which may help reduce the bend radius of stent 50 as it is being deployed from delivery system 10.

In some examples, support member 53 is a proximal support member, and inner member 18 includes a distal support member 82, which extends from distal retaining member 56. Distal support member 82 may be integrally formed with distal portion 38 of the inner member 18, and may be a tubular extension of distal portion 38 that is configured to be received radially within stent 50. Similar to proximal support member 53, distal support member 82 may help prevent a kink point from occurring within catheter 12, such as at the junction of the distal portion 38 of inner member 18 and intermediate portion 19 of inner member 18.

In some examples, proximal support member 53 and distal support member 82 may have substantially similar dimensions; e.g., similar diameters and/or similar lengths. In other examples, the dimensions of proximal support member 53 and distal support member 82 may differ. For example, a diameter of proximal support member 53, which may be formed in stop tube 16, may be greater than a diameter of distal support member 82, which is formed in inner member 18. Such a difference in the dimensions of proximal support member 53 and distal support member 82 may be due to a greater diameter of stop tube 16 relative to inner member 18, which may be configured to accommodate inner member 18 within lumen 34 (shown in FIG. 2) of stop tube 16. However, as with examples in which the dimensions of retaining members 52 and 56 differ, the floor of each of pockets 54, 58A, and 58B also may be equidistant from longitudinal axis 26 relative to the floor of any other one of pockets 54, 58A, and 58B in examples in which the dimensions of support members 53 and 82 differ. Thus, even in examples in which the dimensions of proximal support member 53 and distal support member 82 are different from one another, stent 50 may be retained on catheter 12 in such a manner that stent diameter SD is substantially the same at connecting members 44A, 44B as at connecting members 68A, 68B, which may provide stability to catheter 12 of delivery system 10, thereby improving the ease with which delivery system 10 may be advanced through the vasculature of a patient.

Although a retaining member defining one or more pockets configured to help retain stent 50 in place relative to inner member 18 is described with reference to FIGS. 3A-3C as being defined by stop tube 16, a retaining member may be formed in another structure of catheter 12, such as in the inner member 18.

Figure 4C:
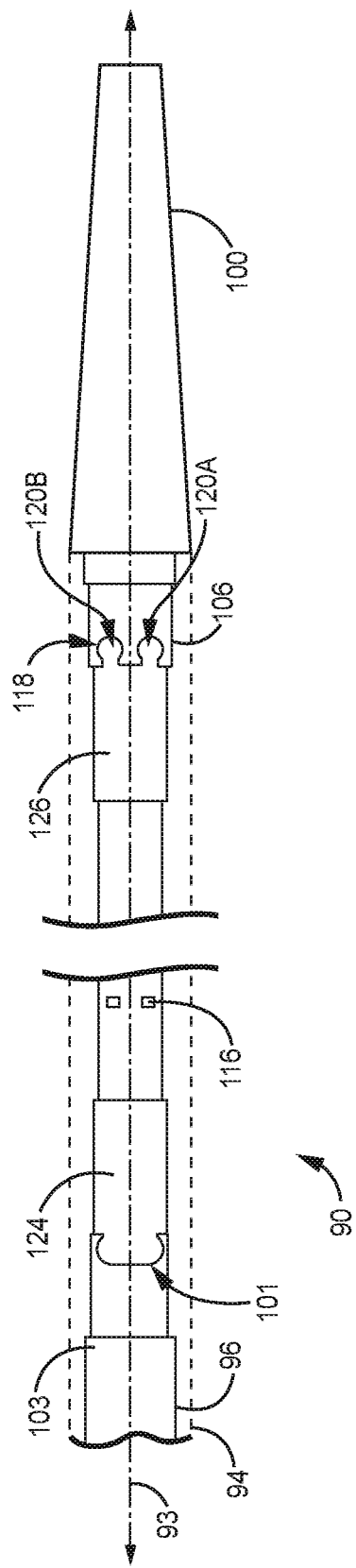
FIG. 4C is a side view of the distal portion of the delivery system of FIGS. 4A and 4B, where an expandable medical device is not received on the delivery system.

FIGS. 4A-4C illustrate a portion of another example delivery system 90 that may be used to deploy stent 50. Delivery system 90 includes a catheter 92, which includes a sheath 94 (shown in phantom), a stop tube 96, an inner member 98, and a distal tip 100. Delivery system 90 may define longitudinal axis 93, which may be a central longitudinal axis of one or more components of delivery system 90 (e.g., of catheter 92). FIG. 4A is a side view of delivery system 90 and illustrates connecting members 44A, 44B of stent 50 received within a retaining member 101 formed in inner member 98. FIG. 4B is a side view of delivery system 90, where stent 50 is shown expanded radially outwardly from retaining member 101 in inner member 98, e.g., during deployment of stent 50 from delivery system 90, and illustrates that inner member 98 further includes a support member 124 received within stent. FIG. 4C is a side view of the distal portion of delivery system 90, where an expandable medical device is not received on delivery system 90 and not included in FIG. 4C.

Stop tube 96 includes a distal portion 103 and defines a lumen configured to receive inner member 98. Inner member 98 includes a distal portion 106, a proximal portion 108, and an intermediate portion 113 positioned between distal portion 106 and proximal portion 108. Retaining member 101 is positioned at proximal portion 108 of inner member 98, and includes at least one pocket 114 configured to receive proximal connecting members 44A, 44B of stent 50. In some examples, inner member 98 also may include intermediate interlocks 116.

One or more features of delivery system 90 of FIGS. 4A-4C may be substantially similar to the corresponding features of delivery system 10 described above with respect to FIGS. 1-3B, and will not be discussed again in detail here. For example, sheath 94, distal tip 100, and intermediate interlocks 116 may be substantially similar to sheath 14, distal tip 22, and intermediate interlocks 72 of delivery system 10, respectively. In some examples, retaining member 101 may be a proximal retaining member 101. In such examples, inner member 98 also may include a distal retaining member 118. Although the example of system 90 shown in FIGS. 4A-4C includes both retaining member 101 and distal retaining member 118, other examples of system 90 may include one of retaining member 101 or distal retaining member 118. In some examples, distal retaining member 118 defines a plurality of pockets, such as a first distal pocket 120A and a second distal pocket 120B that are configured to engage with one or more of distal connecting members 68A, 68B of stent 50. In addition, distal retaining member 118 and distal pockets 120A, 120B may be substantially similar to distal retaining member 56 and distal pockets 58A, 58B of delivery system 10. As with retaining members 52, 56 of delivery system 10, distal portion 106 of inner member 98 at distal retaining member 118 may have an outer dimension (e.g., a diameter) that is substantially the same as an outer dimension (e.g., a diameter) of inner member 98 at proximal retaining member 101, and greater than an outer dimension (e.g., a diameter) of a portion of inner member 98 that is positioned between proximal retaining member 101 and distal retaining member 118. In some examples, the enlarged outer dimension of distal portion 106 of inner member 18 may provide structural support to distal portion 106 of inner member 98 when stent 50 is received on the delivery system 90.

Delivery system 90 may differ from delivery system 10 in that proximal retaining member 101 is formed in inner member 98 instead of in stop tube 96. In the example of FIGS. 4A-4C, distal retaining member 118 defines a first distal pocket 120A and a second distal pocket 120B, each of which may be configured to receive one or more of distal connecting members 68A, 68B of stent 50. As with pockets 54, 58A, and 58B of stop tube 16 and inner member 98, pockets 114, 120A, and 120B extend partially through a thickness of an outer wall of inner member 98 from an outer surface of the outer wall of inner member 98, radially inward toward longitudinal axis 93, to a depth suitable for securely receiving a connecting member (e.g., to a depth $D_R$, described below with respect to FIG. 9B). Because pockets 114, 120A, 120B extend only partially through the thickness of the outer wall of inner member 98, pockets 114, 120A, 120B are partially defined by a floor formed by a material of the outer wall of inner member 98, upon which a portion of stent 50 may be supported when received within pockets 114, 120A, 120B.

Catheter 92 further includes support member 124, which extends from proximal retaining member 101. Support member 124 may be integrally formed with proximal portion 108 of the inner member 98, and may be a tubular extension of proximal portion 108 that is configured to be received radially within stent 50. As illustrated in the side view of FIG. 4B, support member 124 may extend distally within stent 50 past first circumferential row of cells 63 of stent 50 when stent 50 is received on inner member 98. Support member 124 may have a thickness that is less than a thickness of a wall of proximal portion 108 of inner member 98. This difference in thickness of proximal portion 108 of inner member 98 and support member 124 may provide a gradual transition in stiffness between proximal portion 108 and an intermediate portion 113 of inner member 98 (shown in FIG. 4B) that extends between distal portion 106 and proximal portion 108 of inner member 98. In some cases, this gradual transition in stiffness provided by support member 124 may be advantageous to the operation of delivery system 90. As with delivery system 10, the gradual transition in stiffness provided by support member 124 may help prevent a kink point from occurring at the junction of the proximal portion 108 of inner member 98 and intermediate portion 113 of inner member 98. In this way, support member 124 may provide stability to delivery system 90, thereby improving the ease with which delivery system 90 may be advanced through the vasculature of a patient.

In some examples, support member 124 is a proximal support member, and inner member 98 also includes a distal support member 126, which extends from distal retaining member 101. Distal support member 126 may be integrally formed with distal portion 106 of the inner member 98, and may be a tubular extension of distal portion 106 that is configured to be received radially within stent 50. Similar to proximal support member 124, distal support member 126 may provide gradual transition in stiffness between distal portion 106 (which may have a greater stiffness than intermediate portion 113 of inner member 98), and intermediate portion 113 of inner member 98. Such a gradual transition in stiffness may help prevent a kink point from occurring at the junction of the distal portion 106 of inner member 98 and intermediate portion 113 of inner member 98. In this way, support member 126 may provide stability to catheter 92, thereby improving the ease with which delivery system 90 may be advanced through the vasculature of a patient.

In addition, in some cases, it may be advantageous for a proximal retaining member and a support member to be formed in an inner member instead of in a stop tube. For example, delivery systems (e.g., system 90) in which a proximal retaining member and/or a support member are formed in an inner member, instead of in a stop tube, may be simpler and/or less costly to manufacture, and/or be easier for a clinician to use. In some examples, a delivery system may not include a stop tube. Such configurations may reduce a number of components of a delivery system, and/or may reduce a weight of a delivery system. For example, an absence of a stop tube may improve the overall flexibility or trackability of the delivery system, and/or may reduce a profile of the delivery system at a portion of the system proximal to the stent 50.

FIGS. 5A and 5B illustrate a portion of another example delivery system 130 that may be used to deploy the stent 50. Delivery system 130 includes a catheter 132, which includes a sheath 134 (shown in phantom), a stop tube 136, an inner member 138, and a distal tip 140 and defines a longitudinal axis 141. FIG. 5A is a side view of delivery system 130 that illustrates connecting members 44A, 44B of stent 50 received within a retaining member 143 mechanically connected to stop tube 136. FIG. 5B is a side view of delivery system 130, where stent 50 is shown expanding radially outwardly from retaining member 143, e.g., during deployment of stent 50 from delivery system 130, and illustrates that stop tube 136 further includes a support member 144 received within stent. Stop tube 136 includes a distal portion 142, defines a lumen configured to receive inner member 138. In some examples, retaining member 143 may be affixed to distal portion 142 of stop tube 136. Inner member 138 includes a distal portion 148. Retaining member 143 may include a pocket 147, which may be configured to receive proximal connecting members 44A, 44B of stent 50. In some examples, inner member 138 also may include intermediate interlocks 156.

One or more features of delivery system 130 of FIGS. 5A and 5B may be substantially similar to the corresponding features of delivery system 10 described above with respect to FIGS. 1-3C, and will not be discussed again in detail here. For example, sheath 134, distal tip 140, and intermediate interlocks 156 may be substantially similar to sheath 14, distal tip 22, and intermediate interlocks 72 of delivery system 10, respectively. In some examples, retaining member 143 may be a proximal retaining member 143. In such examples, inner member 138 may include a distal retaining member 154. Although the example of system 130 shown in FIGS. 5A-5C includes both retaining member 143 and distal retaining member 154, other examples of system 130 may include one of retaining member 143 or distal retaining member 154. In some examples, distal retaining member 154 defines a first distal pocket 158A and a second distal pocket 158B that are configured to engage with one or more of distal connecting members 68A, 68B of stent 50. Distal retaining member 154 and distal pockets 158A, 158B may be substantially similar to distal retaining member 56 and distal pockets 58A, 58B of delivery system 10. As with retaining members 52, 56 of delivery system 10, distal portion 148 of inner member 138 at distal retaining member 154 may have an outer dimension (e.g., a diameter) that is substantially the same as an outer dimension (e.g., a diameter) of stop tube 136 at proximal retaining member 143.

Delivery system 130 may differ from delivery system 10 in that delivery system 130 includes proximal retaining member 143, is included as an additional structure affixed to stop tube 136, instead of a retaining member formed in a material of stop tube 136. In some examples, proximal retaining member 143 may be fixedly attached to stop tube 136. For example, proximal retaining member 143 may be bonded, crimped, swaged, welded to, embedded in, or otherwise secured to stop tube 136. In other examples, proximal retaining member 143 may be machined, etched, stamped, formed, or otherwise fabricated into the surface of a ring of metal, engineering polymer, ceramic, or other material and the ring applied to stop tube 136 by adhesive bonding, welding, solvent welding, fusing, or any other suitable techniques.

Catheter 132 further includes support member 144, which extends from proximal retaining member 143. Support member 144 may be integrally formed with stop tube 136, and may be a tubular extension of stop tube 136 that extends distally of distal portion 142 of stop tube 136, and is configured to be received radially within stent 50. Similar to support member 53 of stop tube 16 of FIGS. 3A-3C, support member 144 may be integrally formed with stop tube 136, and may be a tubular extension of stop tube 136 that is configured to be received radially within stent 50. As illustrated in the side view of FIG. 5B, support member 144 may extend distally within stent 50 past first row of cells 63 of stent 50 when stent 50 is received on distal retaining member 154 and proximal retaining member 143. In some examples, support member 144 may have a thickness that is less than a thickness of an outer wall of stop tube 136. This difference in thickness between proximal retaining member 143 and support member 144 may provide a gradual transition in stiffness between proximal retaining member 143 and intermediate portion 166 of inner member 138 shown in FIG. 5B. In some cases, this gradual transition in stiffness provided by support member 144 may be advantageous to the operation of delivery system 130, as described above with respect to support members 53 and 124.

In some examples, support member 144 is a proximal support member, and inner member 138 also includes a distal support member 162, which extends from distal retaining member 154. Distal support member 162 may be integrally formed with distal portion 148 of the inner member 138, and may be a tubular extension of distal portion 148 that is configured to be received radially within stent 50. Similar to proximal support member 144, distal support member 162 may provide a gradual transition in stiffness between distal portion 148 and an intermediate portion 166 of inner member 138, which may help prevent a kink point from occurring at the junction of the distal portion 148 of inner member 138 and intermediate portion 166 of inner member 138. In this way, distal support member 162 may provide stability to catheter 132, thereby improving the ease with which delivery system 130 may be advanced through the vasculature of a patient.

The retaining members of any of the example delivery systems described above may engage with the connecting members of a stent (e.g., connecting members 68A, 68B and 44A, 44B of stent 50) by any suitable technique. For example, a pocket of a retaining member of an example delivery system may be a mating structure configured to mechanically engage with one or more connecting members of a stent by forming an interlocking mating connection with the one or more connecting members. Such an interlocking mating connection between a pocket of a retaining member and one or more connecting members of a stent may enable the stent to be securely coupled to a catheter on which the retaining member is positioned until the stent is deployed at a treatment site. As described below with respect to FIGS. 6A-6N, a pocket of a retaining member may have any suitable configuration for mechanical engagement with a connecting member of a stent.

Figure 6A:
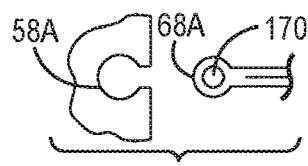
FIGS. 6A-6N are side views of example connecting members and corresponding example retaining members of the stents described herein.
Figure 6B:
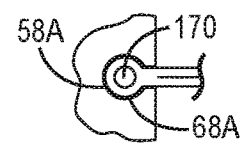
Figure 6C:
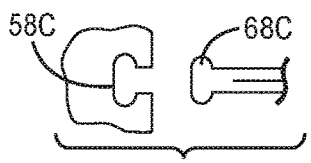
Figure 6D:
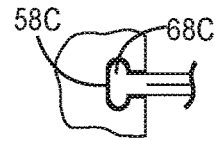
Figure 6E:
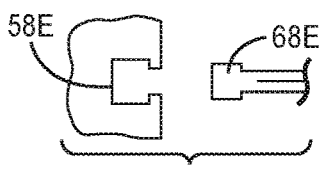
Figure 6F:
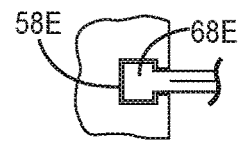
Figure 6G:
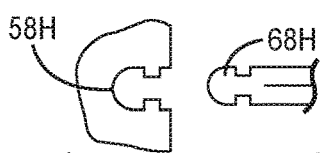
Figure 6H:
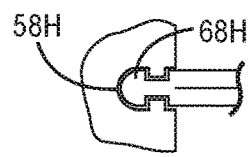
Figure 6I:
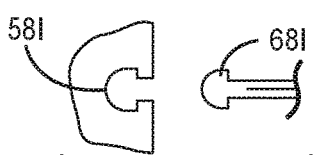
Figure 6J:
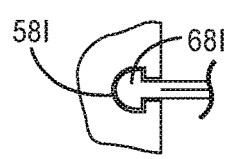
Figure 6K:
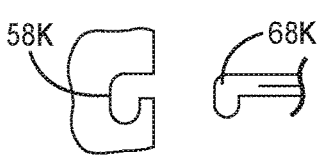
Figure 6L:
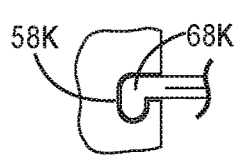
Figure 6M:
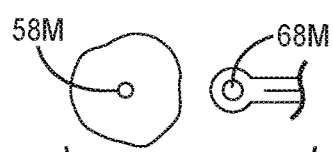
Figure 6N:
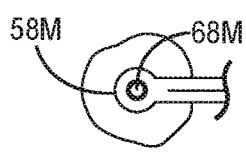

FIGS. 6A-6N are side views of example configurations of connecting members and corresponding example retaining members that may be used with any of delivery systems 10, 90, and 130. The examples of FIGS. 6A-6N illustrate seven example configurations that a pairing between any of pockets 58A, 58B, and 54 of delivery system 10, and one or more of connecting members 68A, 68B, 44A, and 44B may include. In the first figure of each of the paired FIGS. 6A-6B, 6C-6D, 6E-6F, 6G-6H, 6I-6J, 6K-6L and 6M-6N (e.g., FIG. 6A), the example pocket (e.g., pocket 58A) and the corresponding connecting member (e.g., connecting member 68A) are shown disengaged from one another. In the second figure of each the paired figures, (e.g., FIG. 6B), the pocket (e.g., pocket 58A) and the corresponding connecting member (e.g., connecting member 68A) are shown interlocked with the connecting member received within the pocket.

As shown in FIGS. 6A-6N, the shape of a pocket and the shape of a corresponding connecting member are configured to mechanically interfere with proximal or distal movement of connecting members (e.g., connecting member 68A) relative to the corresponding pocket (e.g., pocket 58A) when the connecting member 68A is received within pocket 58A. For example, an enlarged portion of connecting member 68A may be configured to fit within pocket 58A, but mechanically interfere with proximal or distal movement (e.g., relative to catheter 12) of connecting member 68A. This mechanical interference between connecting member 68A and pocket 58A may help retain connecting member 68A within pocket 58A during delivery of stent 50 to a treatment site within the vasculature of a patient, but still allow radially outward movement (e.g., relative to central longitudinal axis 26 of delivery system 10) of connecting member 68A out of pocket 58A when sheath 14 is retracted proximally past connecting member 68A.

In some examples, the shapes of the connecting members and pockets of the retaining members of FIGS. 6A-6N may be circular, semi-circular, oblong, oval, rectangular, L-shaped, or any combination of several such shapes. For example, the pockets of the retaining members of FIGS. 6A-6N may be recessed regions within the respective retaining members. In other examples, a pocket (e.g., pocket 58M shown in FIG. 6M) may be a recessed region configured to receive a pin or other protrusion extending from a surface of a connecting member (e.g., connecting member 68M shown in FIG. 6N). In such examples, when a pin or other protrusion of connecting member 68M is received within pocket 58M, a portion of connecting member 68M that does not include the pin or other protrusion may be supported on surface 36 of stop tube 16. However, the shapes of the connecting members and retaining members shown in FIGS. 6A-6N are merely illustrative and not meant to limit the scope of the invention.

In some examples, a configuration of a connecting member and a configuration of a corresponding retaining member may be selected based on a desired degree of mechanical interference between the connecting member and the corresponding retaining member. In other examples, a configuration of a connecting member and a corresponding retaining member may be selected to include one or more radiopaque markers. For example, as illustrated in FIGS. 6A and 6B, connecting member 68A includes one or more markers 170. Markers 170 may be one or more radiopaque markers or ultrasonic (e.g., echogenic) markers, such as may permit a clinician to accurately determine the position of stent 50 within the patient's lumen under fluoroscopic or ultrasonic visualization during a medical procedure to deploy stent 50 within a target vessel of the patient. In another example, markers 170 may be one or more MRI safe markers that permit a clinician to accurately determine the position of stent 50 within the vasculature of a patient under magnetic resonance imaging. In examples in which markers 170 are one or more of ultrasonic or MRI-safe markers, the use of ultrasonic and MRI visualization may be used to visualize position and condition of stent 50 during non-invasive follow-up and monitoring.

In some examples, markers 170 may be positioned on one or more of the connecting members (e.g., connecting member 68A of FIGS. 6A and 6B) of stent 50 by techniques such as adhesive, beat fusion, interference fit, fasteners, intermediate members or other any other suitable technique. In some examples, a connecting member may define an opening in the form of a hole or aperture (e.g., a hole extending through the connecting member) within which one or more of markers 170 may be positioned. For example, markers 170 may be in the form of insert pieces that can be press-fit or riveted within the holes or apertures of the connecting member.

In examples in which markers 170 are radiopaque, materials for making the markers 170 should have a density suitable for visualization through fluoroscopic techniques. Preferably, the markers 170 may have a radiopacity that is substantially greater than a radiopacity of the material forming the rest of stent 50. Example radiopaque materials for use with fluoroscopic visualization may include tantalum, platinum, gold, tungsten and alloys of such metals. In some examples, markers 170 may be coated with a radiopaque material, or may be filled with radiopaque material.

In examples in which markers 170 are configured for use with ultrasonic visualization, materials for making markers 170 may have an acoustical density that is sufficiently different from an acoustical density of the rest of stent 50 to provide suitable visualization through ultrasonic techniques. Example materials for use with ultrasonic visualization may include polymers (for metallic stents), metals such as tantalum, platinum, gold, tungsten and alloys of such metals (for polymeric or ceramic stents), hollow glass spheres or microspheres, and other suitable materials. In examples in which markers 170 are MRI-safe, the materials for making markers 170 may be non-ferrous, and may have a magnetic signature that is sufficiently different from a magnetic signature of the rest of stent 50 to provide suitable visualization through MRI techniques. Example materials for MRI visualization may include polymers (for metallic stents), metals such as tantalum, platinum, gold, tungsten and alloys of such metals (for polymeric or ceramic stents), and other suitable materials.

Figure 7:
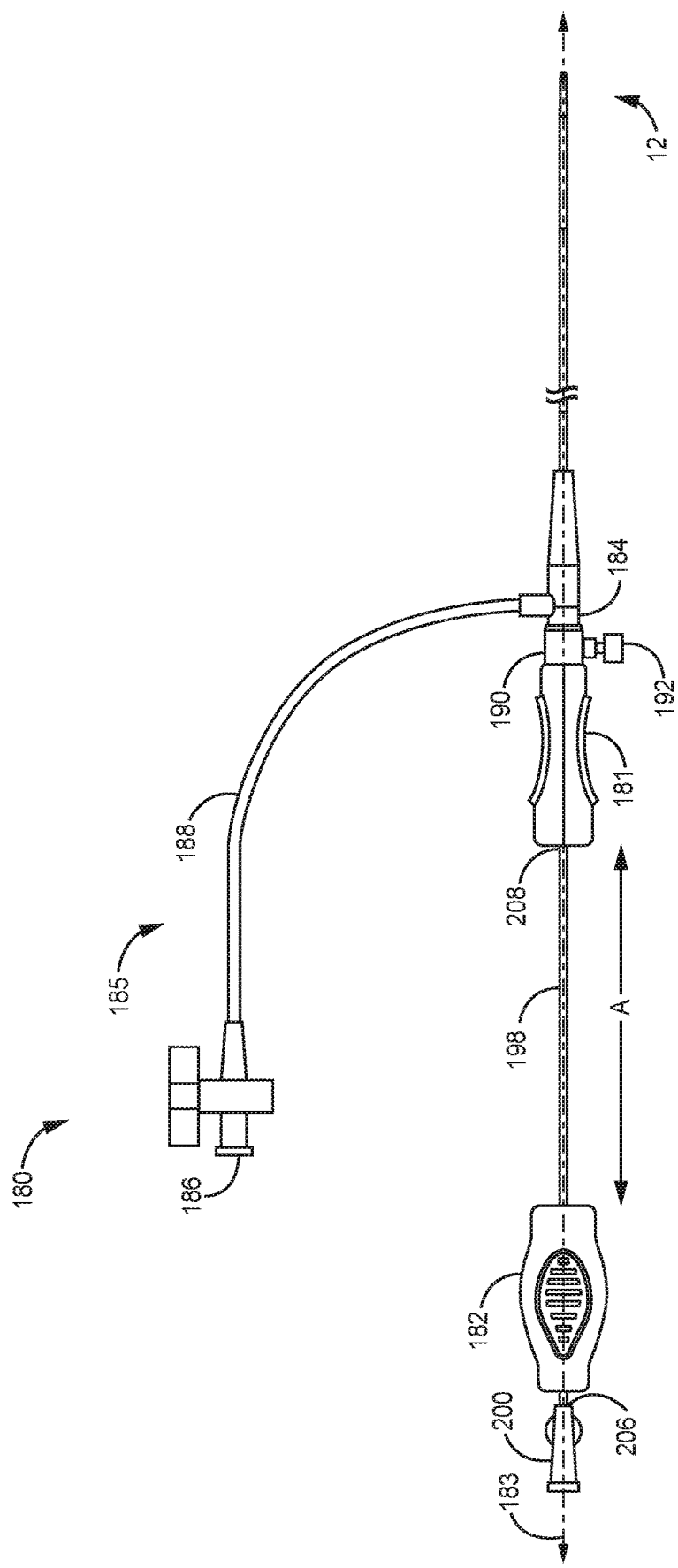
FIG. 7 is a side view of an example delivery system that includes the catheter of FIG. 1, and first and second handles.
Figure 8:
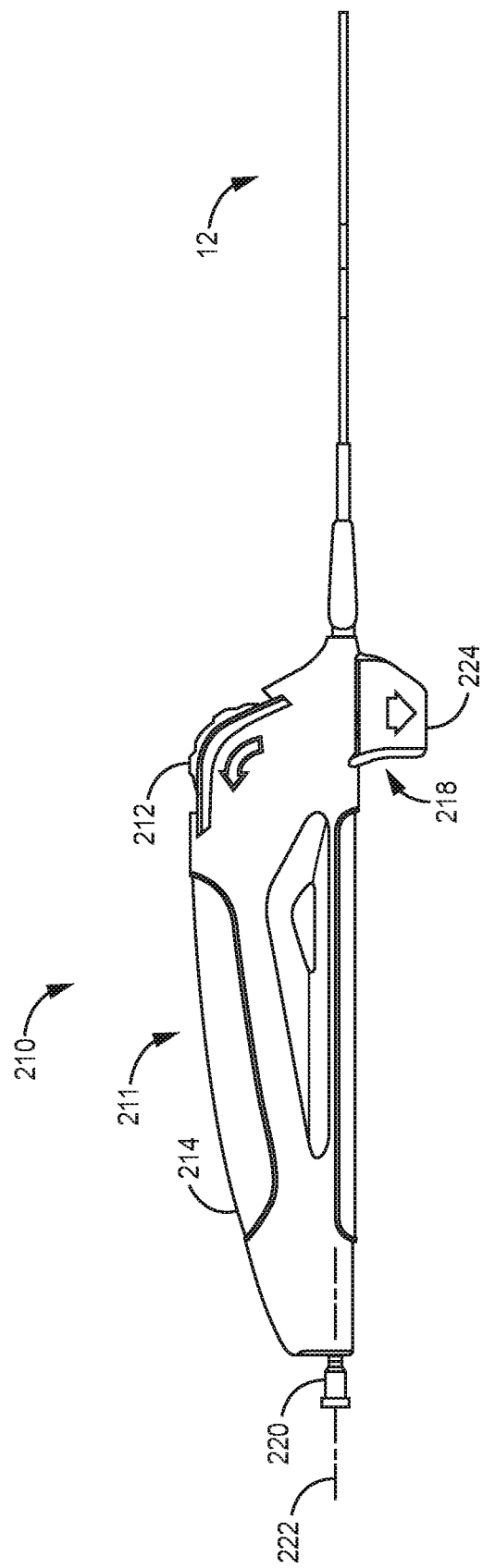
FIG. 8 is a side view of another example delivery system that includes the catheter of FIG. 1 and a handle including a thumbwheel.

FIGS. 7 and 8 are side views of example delivery systems that may be used with any of the catheters of FIGS. 1-5B to introduce and deploy an expandable medical device (e.g., a stent), into a vessel within a body of a patient. FIG. 7 is a side view of delivery system 180 that includes catheter 12 of FIG. 1, a first handle 181, and a second handle 182. In addition to catheter 12, delivery system 180 of FIG. 7 defines a longitudinal axis 183, and includes a strain relief jacket 184, a manifold housing 185, and an admission port 186 in fluid communication with the manifold housing 185 via a fluid transfer line 188. In addition, delivery system 180 further includes a lock housing 190, a threaded locking member 192, a first handle 181, a second handle 182, a reinforcing member 198, and a port housing 200 connected to the reinforcing member 198. In the example of catheter 12, manifold housing 185 may be connected to a proximal portion of sheath 14 of catheter 12, and strain relief jacket 184 may be positioned around the proximal portion of sheath 14.

Strain relief jacket 184 may be configured to disperse forces experienced by the proximal portion of sheath 14 where sheath 14 meets manifold housing 185 to help maintain the integrity of a connection between the proximal portion of sheath 14 and manifold housing 185. Proximal portion 40 of inner member 18 of catheter 12 may be partially received within manifold housing 185 and lock housing 190, such that an interior of manifold housing 185 is in fluid communication with a passage that extends between inner member 18 and sheath 14 (i.e., a space between inner member 18 and sheath 14). In such examples, a fluid, such as a contrast medium, may be introduced into admission port 186 directed through transfer line 188 and an interior of the manifold housing 185 to the passage, which may be a space between sheath 14 and inner member 18. The fluid then may be directed from the passage into a lumen of a target vessel within the body of a patient.

As shown in FIG. 7, reinforcing member 198 comprises an elongate body configured to extend distally from port housing 200, through each of handles 181, 182, and into manifold housing 185 when delivery system 10 is in the assembled configuration shown in FIG. 7. In some examples, reinforcing member 198 may define a lumen (not shown), a proximal end 206, and a distal portion 208. Port housing 200, which may be positioned at a proximal end 206 of reinforcing member 198, may form an inlet configured to permit access to inner member 18 via lumen 204 of reinforcing member 198. Handles 181, 182 provide structures that a clinician may use to grasp delivery system 180 and advance or retract sheath 14 over inner member 18 and stop tube 16.

In the example of FIG. 7, first handle 181 may be positioned over reinforcing member 198 at distal portion 208 of reinforcing member 198, and second handle 182 may be positioned over reinforcing member 198 proximally of first handle 181. Lock housing 190 includes threaded locking member 192, which can be turned to engage reinforcing member 198 and to selectively permit or inhibit axial movement between inner member 18 and sheath 14. For example, when threaded locking member 192 is engaged with reinforcing member 198, threaded locking member 192 inhibits movement (e.g., longitudinal movement along longitudinal axis 183) between inner member 18 and sheath 14, whereas movement between inner member 18 and sheath 14 is permitted when threaded locking member 192 is disengaged from reinforcing member 198. The relative movement of the inner member 18 and sheath 14 may be initiated during the deployment of a stent at a target site within a vessel of a patient by disengaging threaded locking member 192 from reinforcing member 198, thereby allowing retraction or advancement of sheath 14 to expose or cover a stent or another expandable medical device that may be positioned on inner member 18 and/or stop tube 16.

First handle 181 and second handle 182 are configured to be grasped by a user and moved relative to one another to cause retraction or advancement of sheath 14 relative to inner member 18. In some examples, handles 181, 182 may be mechanically attached to lock housing 190 and reinforcing member 198, respectively. In the configuration shown in FIG. 7, handles 181, 182 are axially spaced apart from one another with respect to longitudinal axis 183, and sheath 14 is extended distally to cover inner member 18, thereby preventing deployment of a stent or other expandable medical device positioned on inner member 18. When handles 181, 182 are moved toward one other, (e.g., when second handle 182 is moved distally toward first handle 181 or first handle 181 is moved proximally toward second handle 182), sheath 14 slides proximally relative to inner member 18. In other words, the relative movement between handles 181, 182 (represented by arrow "A") results in relative movement (e.g., longitudinal movement along longitudinal axis 183) between inner member 18 and sheath 14. When handles 181, 182 are moved toward one other and sheath 14 slides proximally relative to the inner member 18, stent 50 mounted on inner member 18 may be exposed, such that a stent may freely expand off from inner member 18 from a compressed configuration to an expanded configuration.

After such expansion, delivery system 180 may be retracted proximally of the expanded stent and removed from the body of the patient.

Inner member 18 and sheath 14 may have sufficient rigidity to permit catheter 12 of delivery system 180 to be advanced through the vasculature of a patient without buckling, yet have sufficient flexibility to conform to the curvature of tortuous portions of the vasculature of the patient. In addition, distal tip 22 may have greater flexibility than inner member 18 or sheath 14, such that distal tip 22 may yield when contacting a wall of a vessel. The components of delivery system 180 may be formed from any suitable biocompatible materials. In some examples, one or more of stop tube 16, inner member 18, and sheath 14 may be formed from a suitable polymer, such as, but not limited to polyether ether ketone (PEEK), polytetrafluoroethylene (PTFE), a polyamide, a polyether block amide (e.g., PEBAX), a polyurethane, a polyethylene, vinyl, expanded-polytetrafluoroethylene (ePTFE), a polyamide, a fluoropolymer, or other polymers. In addition, or instead, one or more of stop tube 16, inner member 18, sheath 14, or distal tip 22 may include one or more other materials, such as a stainless steel or another biocompatible metal. In other examples, one or more components of delivery system 10 may include a material that may be visualized during fluoroscopy, such as a nickel-titanium alloy (e.g., Nitinol), or another suitable radiopaque material.

FIG. 8 is a side view of another example delivery system 210 that includes catheter 12 of FIG. 1, and a handle 211 including a thumbwheel 212. As with delivery system 180 of FIG. 7, delivery system 210 is configured for use in a medical procedure to introduce and deploy an expandable medical device (e.g., a stent), into a target vessel within a body of a patient. In addition to catheter 12, delivery system 210 includes a handle 211. Handle 211 may include, for example, a handle body 214, a thumbwheel 212, a lock member 218, and a port housing 220, and may define a longitudinal axis 222. In some examples, one or both of inner member 18 and stop tube 16 of catheter 12 may extend through handle body 12, such that inner member 18 or stop tube 16 may be secured to port housing 220, thereby securing inner member 18 or stop tube 16 relative to longitudinal axis 222 such that the inner member 18 or the stop tube 16 may remain substantially stationary when sheath 14 is advanced or retracted. In some examples, adhesives, cements, glues, welding connections, thermal bonding or insert molding techniques may be used to secure one or both of inner member 18 and stop tube 16 to port housing 220.

Thumbwheel 212 illustrated in FIG. 8 is rotatably mounted to handle body 214 and provides an actuator for sheath 14 of delivery system 210. During delivery of an expandable medical device, such as a stent, via delivery system 210, rotation of thumbwheel 212 by a clinician causes a pull cable (not shown) that is attached to the sheath 14 within handle body 214 to retract sheath 14 in a proximal direction to uncover and release an expandable medical device that may be positioned on inner member 18 or stop tube 16.

Lock member 218, which may be releasably mountable to handle body 214, is configured to selectively permit or inhibit rotation of thumbwheel 212 and resulting movement (e.g., longitudinal movement along longitudinal axis 222) of sheath 14 relative to inner member 18 and stop tube 16. For example, when lock member 218 is mounted on handle body 214, one or more portions of lock member 218 may engage thumbwheel 212 and inhibit rotation of thumbwheel 212. In some examples, lock member 218 includes a tab 224, which may provide a grasping surface for a clinician or other user to grasp lock member 218 to mount or release lock member 218 with respect to handle body 214.

FIGS. 9A-14B illustrate various example configurations of the retaining members and support members that may be used in conjunction with one or more components of delivery systems 10, 90, and 130 described above with respect to FIGS. 1-5B. Although the retaining members and support members described below with respect to FIGS. 9A-14B are described as being formed in or extending from the stop tubes of the delivery systems of FIGS. 1-5B, any of the retaining members and support members of FIGS. 9A-14B may be formed in or extend from other components of the delivery systems of FIGS. 1-5B. For example, the retaining members and support members of FIGS. 9A-14B may be formed in or extend from an inner member of such systems, which may, in some examples, be inner member 18 of delivery system 10 or inner member 98 of delivery system 90. As another example, the retaining members and support members of FIGS. 9A-14B may be formed in a structure separate from a stop tube or an inner member, such as proximal retaining member 143 of delivery system 130, which may be connected to a stop tube or an inner member.

Figure 9A:
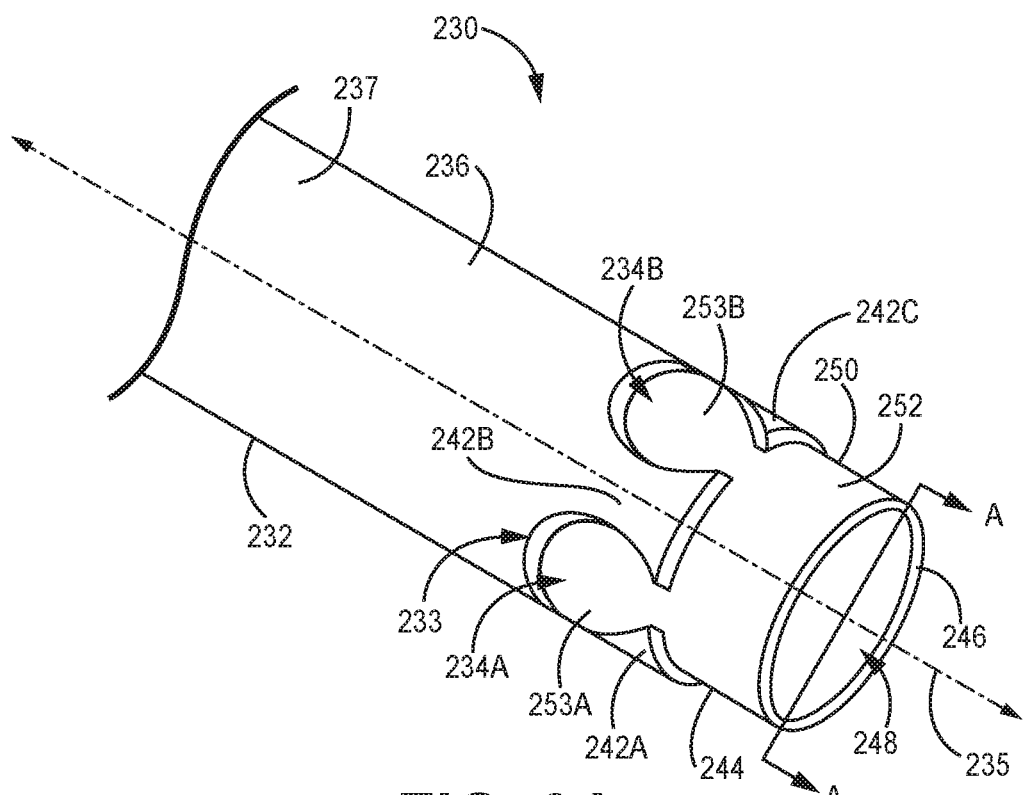
FIG. 9A is a perspective view of a portion of another example delivery system, and illustrates an example retaining member that defines a plurality of pockets, where the delivery system includes a single support member.
Figure 9B:
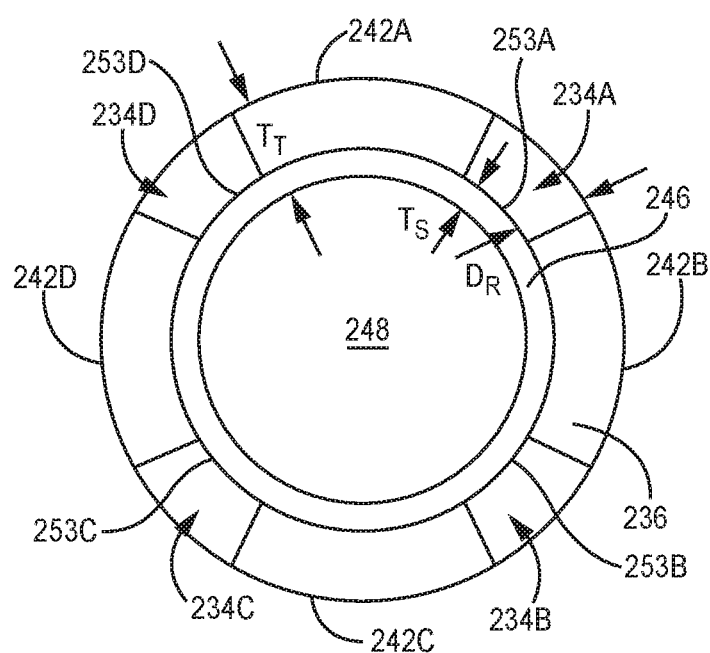
FIG. 9B is an end view of the portion of the delivery system of FIG. 9A.
Figure 9C:
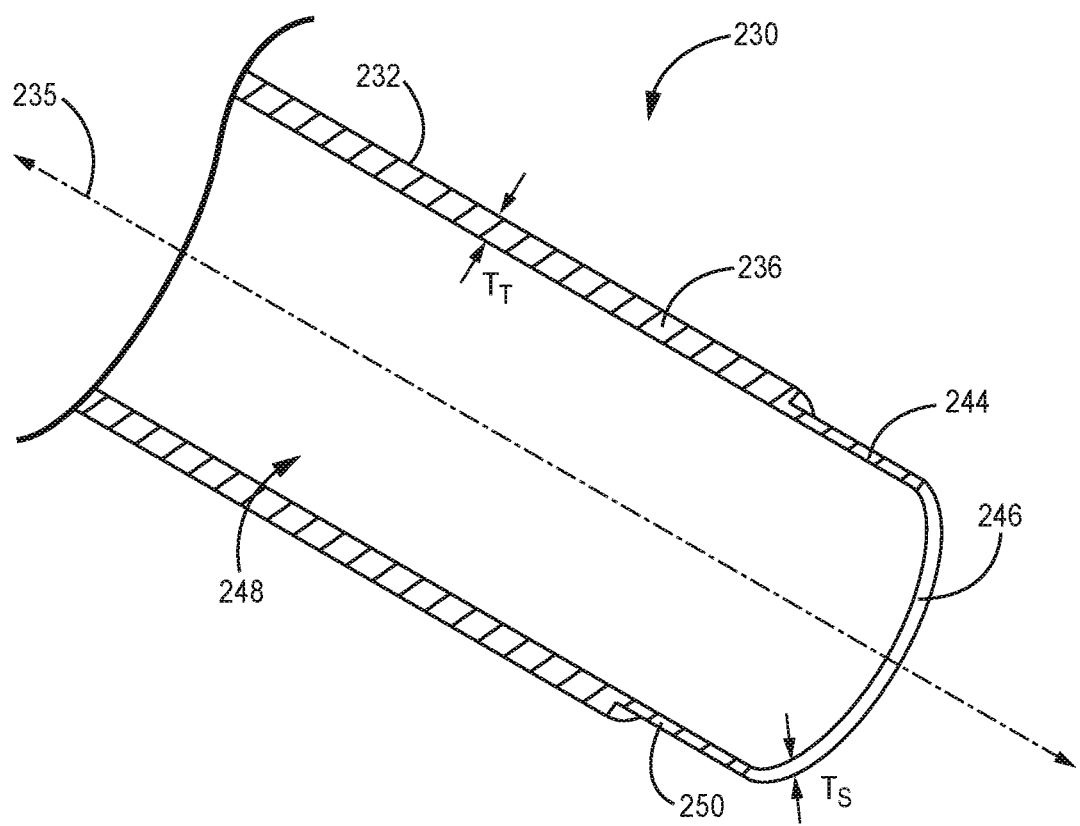
FIG. 9C is a cross-sectional perspective view of the portion of the delivery system of FIG. 9A, where the cross-section is taken along line A-A of FIG. 9A and along a longitudinal axis of the delivery system.

FIGS. 9A-9C illustrate a portion of another example delivery system 230 that can be used to deploy stent 50 and which includes a stop tube 232 that defines a longitudinal axis 235. Longitudinal axis 235 may be a longitudinal axis both of delivery system 230 and stop tube 232. FIG. 9A is a perspective view of the portion of delivery system 230, and illustrates a retaining member 233 that defines a plurality of pockets 234A and 234B. FIG. 9B is an end view of the portion of the delivery system 230 of FIG. 9A, which illustrates that retaining member 233 further defines pockets 234C and 234D. As shown in FIG. 9B, stop tube 232 further includes wall segments 242A, 242B, 242C, and 242D that extend between corresponding ones of pockets 234A-234D, and which form portions of retaining member 233. FIG. 9C is a cross-sectional view of the portion of the delivery system 230 of FIG. 9A, where the cross-section is taken along line A-A of FIG. 9A and along longitudinal axis 235.

In the example of FIG. 9A, stop tube 232 has an outer wall 236 that includes a retaining member 233. Stop tube 232 further includes a tubular support member 244 that includes a distal end 246. Support member 244 extends distally of pockets 234A-234D of stop tube 232, and defines a lumen 248 configured to receive an inner member, such as inner member 18 of the delivery system 10. Support member 244 includes an outer wall 250 having an outer surface 252, which also may form a floor of pockets 234A-234D as described below.

Many of the features of delivery system 230 may be substantially similar to the components of delivery systems 10 of FIGS. 1, 3A, 3B, and 3C. For example, example delivery system 230 may include inner member 18, sheath 14, and distal tip 22 of delivery system 10. In other examples, one or more of the features of delivery system 230 may be substantially similar to the components of delivery system 90 of FIGS. 4A-4C. In such examples, pockets 234A-234D of delivery system 230 may be formed in an outer wall of an inner member of delivery system 230, and delivery system 230 may include stop tube 96 of FIGS. 4A-4C. For the sake of brevity, however, delivery system 230 will be described as having pockets 234A-234D formed in outer wall 236 of stop tube 232.

Pockets 234A-234D may be spaced in various configurations relative to one another and relative to wall segments 242A-242D of stop tube 232. In the example shown in FIG. 9B, pockets 234A-234D are formed in outer wall 236 of stop tube 232 and spaced about longitudinal axis 235 of stop tube 232. Pockets 234A-234D may be formed in outer wall 236 of stop tube 232 using any suitable technique, such as, but not limited to, molding, laser etching, or by using a mechanical cutting technique. In the illustrated example of FIG. 9A, each of pockets 234A and 234B have substantially the same shape as pocket 54 illustrated in FIGS. 3A-3C. Although not shown in FIG. 9A, pockets 234C and 234D also may have substantially the same shape as pocket 54 illustrated in FIGS. 3A-3C. In other examples, however, pockets 234A-234D may have different shapes than those of pockets 234A and 234B illustrated in FIG. 9A, such as any of the shapes of the retaining members illustrated in FIGS. 6C-6N, or any other suitable shapes not depicted herein.

In some examples, outer surface 252 of outer wall 250 of support member 244 may provide floors 253A-253D of ones of pockets 234A-234D, such that a connecting member of a stent (e.g., one or more of connecting members 44A, 44B, 68A, or 68B, of stent 50) may be supported on outer surface 252 within one of pockets 234A-234D when stent 50 is received on stop tube 232. Thus, floors 253A-253D of corresponding ones of pockets 234A-234D may form a substantially continuous surface with the portion of outer surface 252 of outer wall 250 of support member 244 that extends distally of pockets 234A-234D, such that the connecting members of stent 50 may be evenly supported within pockets 234A-234D.

In the example of FIGS. 9A-9C, the configuration (e.g., the shape and/or dimensions) of each of pockets 234A-234D are substantially the same (e.g., the same except for minor manufacturing variances), and pockets 234A-234D are substantially equally spaced apart from one another such that the configuration and dimensions of each of wall segments 242A-242D are substantially equal. In other examples, e.g., examples in which stop tube 232 has a substantially circular cross-section, pockets 234A-234D may be circumferentially offset or diametrically opposed from another pocket. The spacing of pockets 234A-234D may depend upon one or more considerations, such as a spacing of the corresponding connecting members 68A, 68B, and 44A, 44B of stent 50. In addition, although four pockets 234A-234D and four wall segments 242A-242D are described with respect to the example of FIGS. 9A-9C, stop tube 232 may include a greater or fewer number of pockets 234A-234D, and a correspondingly greater or fewer number of wall segments 242A-242D. For example, the number of pockets and wall segments of stop tube 232 may be based on the number of connecting members of a stent configured to be received on stop tube 232.

Pockets 234A-234D may have any of a variety of shapes. For example, a shape of one or more of pockets 234A-234D (e.g., a perimeter of pockets 234A-234D as defined by outer wall 236 of stop tube 232) may be a substantially round shape, as shown in FIG. 9A. In other examples, a shape of one or more of pockets 234A-234D may be an oblong shape, a substantially rectangular shape, or any other suitable shape. In some examples, each of pockets 234A-234D may have substantially the same shape, whereas in other examples, one or more of pockets 234A-234D may have a different shape from any other one of pockets 234A-234D. In any such examples, the shapes of pockets 234A-234D may be selected based on one or more considerations, such as a desired degree of security of the reception of connecting members 68A, 68B, 44A, and 44B within pockets 234A-234D.

As illustrated in FIG. 9A, tubular support member 244 may extend distally of pockets 234A and 234B, and wall segments 242A-242C. Tubular support member 244 may be substantially similar to support member 53 described above with respect to FIGS. 3A-3C. For example, tubular support member 244 may be formed integrally with stop tube 232. In some examples, tubular support member 244 of FIGS. 9A-9C is an extension of stop tube 232 that is configured to be received radially within stent 50. In some examples, tubular support member 244 may extend distally within stent 50 past first row of cells 63 of stent 50 when stent 50 is received on inner member 18 and stop tube 232. As described below with respect to FIGS. 9B and 9C, support member 244 may have a thickness that is less than a thickness of a wall of stop tube 232. This difference in thickness of stop tube 232 and support member 244 may provide a gradual transition in stiffness between stop tube 232 and inner member 18. In some cases, this gradual transition in stiffness provided by support member 244 may be advantageous to the operation of delivery system 230, as described above with respect to support member 53 of the delivery system 10, and may allow a clinician to perform a medical procedure with greater ease and efficiency.

The end view of stop tube 232 illustrated in FIG. 9B provides a view of stop tube 232 looking parallel with longitudinal axis 235 of stop tube 232 from distal end 244 of support member 244. Lumen 248 of stop tube 232 is shown in this view, as are each of pockets 234A-234D and wall segments 242A-242D. As shown in FIG. 9B, outer wall 236 of stop tube 232 may have a total thickness $T_T$. A perimeter of each of pockets 234A-234D is defined by an outer surface 237 of outer wall 236. Each of pockets 234A-234D may extend partially through a thickness of outer wall 236 from outer surface 237, radially inward toward central longitudinal axis 235, to a depth $D_R$, which is suitable for securely receiving one or more of connecting members 68A, 68B, 44A, or 44B of stent 50. In the example of FIG. 9B, depth $D_R$ of pockets 234A-234D may be about 25% to about 75% of a total thickness $T_T$ of outer wall 236, although other depths $D_R$ of pockets 234A-234D are possible. Depth $D_R$ of pockets 234A-234D may be selected based on a thickness of one or more of connecting members 68A, 68B, 44A, and 44B of stent 50, thereby enabling pockets 234A-234D to securely receive one or more of connecting members 68A, 68B, 44A, and 44B. Because pockets 234A-234D each extend only partially through the thickness of outer wall 236, pockets 234A-234D each are partially defined by a corresponding floor 253A-253D formed by a material of outer wall 236, upon which a portion of stent 50 (e.g., one or more of connecting members 68A, 68B, 44A, and 44B) may be supported when received within pockets 234A-234D.

In some examples, the depth $D_R$ of pockets 234A-234D may correspond to about 25% to about 100% of a thickness of one or more of connecting members 68A, 68B, 44A, and 44B of stent 50. Depth $D_R$ of pockets 234A-234D also may be selected based on a desired degree of security of the reception of connecting members 68A, 68B, 44A, and 44B within pockets 234A-234D. For example, in examples in which the depth $D_R$ of pockets 234A-234D corresponds to a relatively high percentage of a thickness of connecting members 68A, 68B, 44A, and 44B, (e.g., from about 75% to about 100%), connecting members 68A, 68B, 44A, and 44B may be more securely retained within pockets 234A-234D than examples in which depth $D_R$ of pockets 234A-234D corresponds to a relatively low percentage of a thickness of the connecting members 68A, 68B, 44A, and 44B, (e.g., from about 25% to about 50%). Thus, in examples in which a relatively more secure connection between connecting members 68A, 68B, 44A, and 44B and pockets 234A-234D is desired, such as examples in which stent 50 is compressed to a relatively high degree when in the compressed configuration, depth $D_R$ of pockets 234A-234D may correspond to relatively high percentage of a thickness of connecting members 68A, 68B, 44A, and 44B.

As also shown in FIG. 9B, outer wall 250 of support member 244 may have a thickness $T_S$. Thickness $T_S$ of outer wall 250 of support member 244 is less than total thickness $T_T$ of outer wall 236 of stop tube 232 proximal to support member 244, by depth $D_R$ of pockets 234A-234D. Although not shown in FIG. 9B, a portion of outer wall 236 of the stop tube 232 at pockets 234A-234D also may have thickness $T_S$. In some examples, depth $D_R$ may be from about 0.20 mm to about 0.64 mm and the thickness $T_S$ may be from about 0.07 mm to about 0.39 mm, such that total thickness $T_T$ of outer wall 236 may be from about 0.28 mm to about 1.02 mm.

The cross-sectional view of stop tube 232 of FIG. 9C illustrates the relationship between thickness $T_S$ of support member 244 and thickness $T_T$ of outer wall 236 of the stop tube 232 proximal to support member 244. As shown in FIG. 9C, thickness $T_S$ of outer wall 250 of support member 244 is substantially constant along a length of support member 244 measured parallel to longitudinal axis 235. In some examples, as described above, outer wall 250 of support member 244 and outer wall 236 of stop tube 232 may be integrally formed. In other examples, such as the example illustrated in FIG. 9C, outer wall 250 of support member 244 may be formed separately from outer wall 236 of stop tube 232. In such examples, outer wall 236 of stop tube 232 may be formed with pockets 234A-234D molded, cut, or etched therein by any of the means described above, after which the outer wall 250 of support member 244 and outer wall 236 of stop tube 232 may be affixed together, such as by welding, adhesives, or other techniques.

Figure 10A:
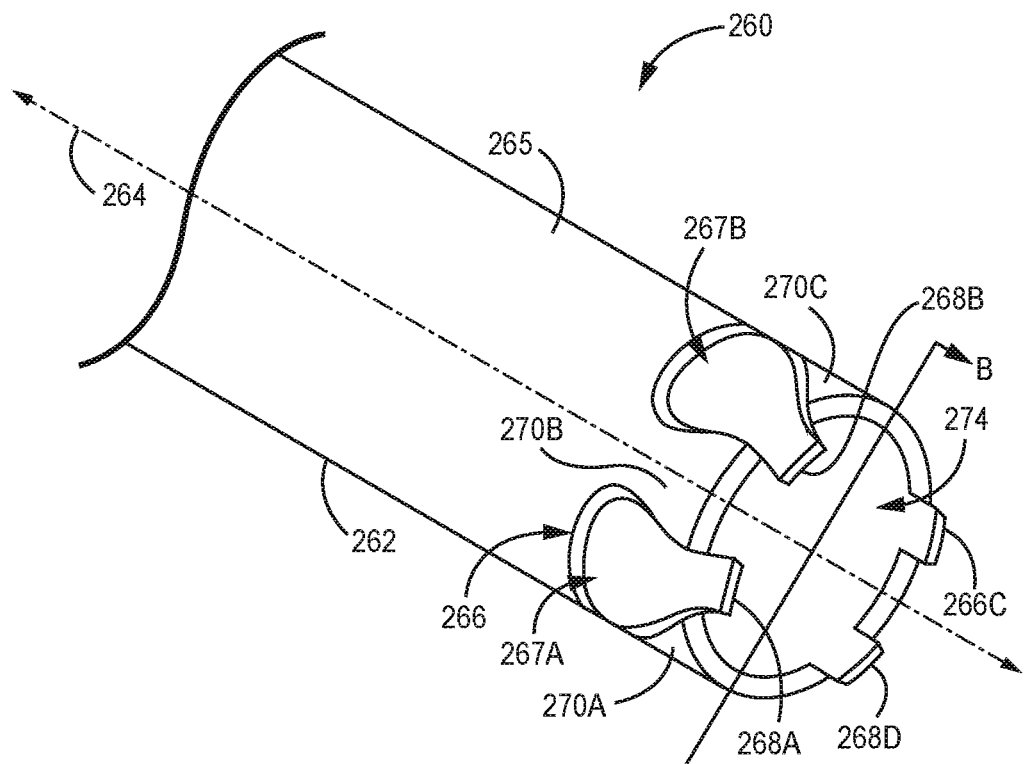
FIG. 10A is a perspective view of a portion of another example delivery system, and illustrates an example retaining member that defines a plurality of pockets, where the delivery system includes a plurality of support members.
Figure 10B:
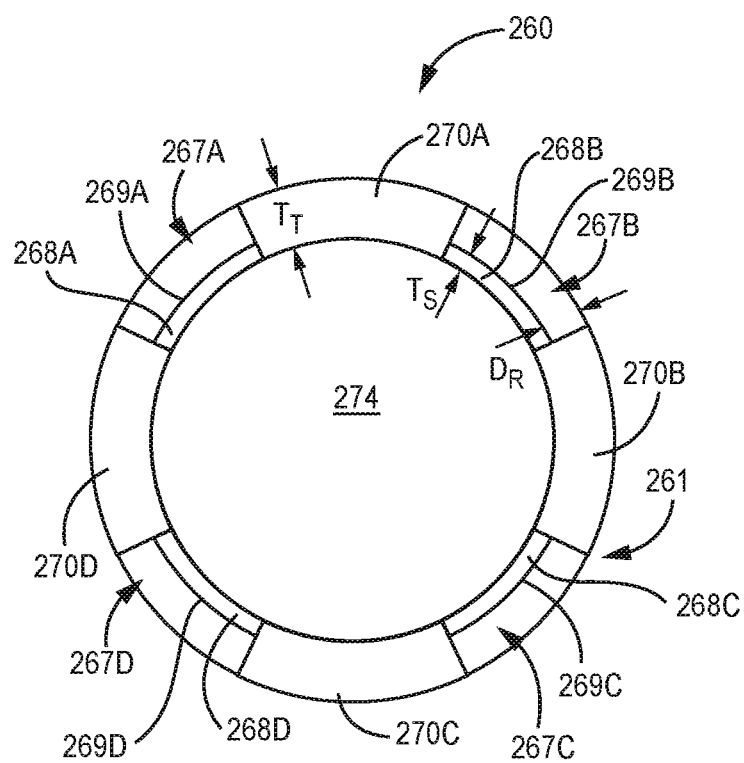
FIG. 10B is an end view of the portion of the delivery system of FIG. 10A.
Figure 10C:
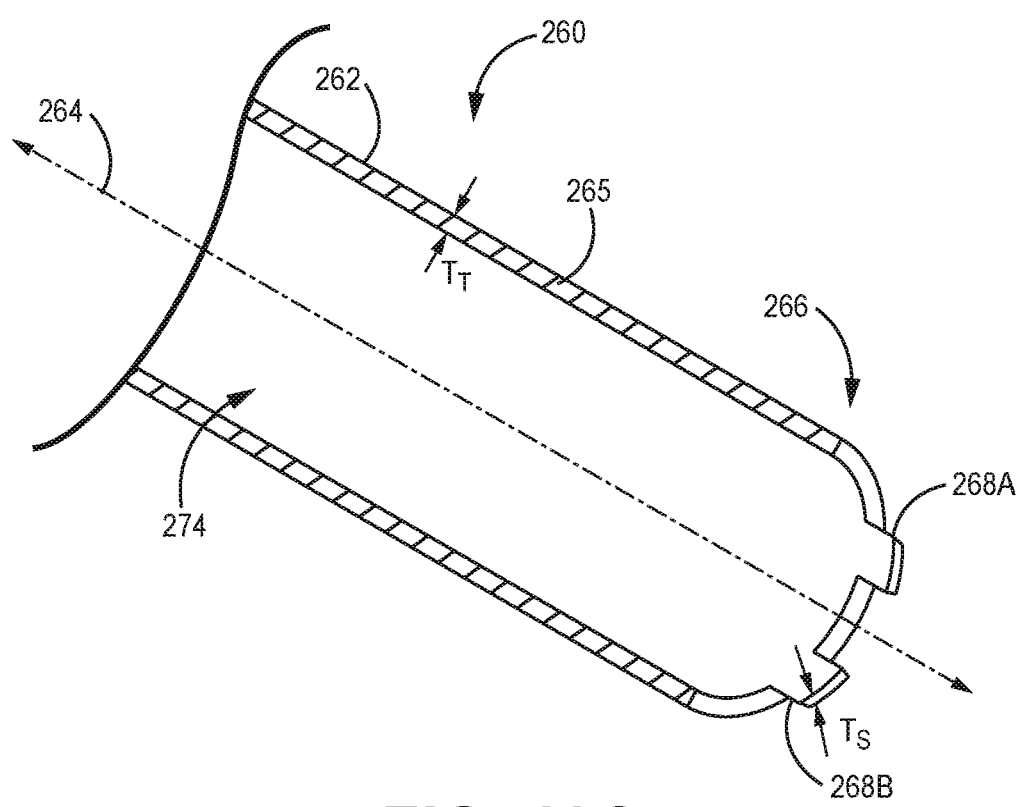
FIG. 10C is a cross-sectional perspective view of the portion of the delivery system of FIG. 10A, where the cross-section is taken along line B-B of FIG. 10A and along a longitudinal axis of the delivery system.

In some examples, support members of an inner member or a stop tube may have configurations that differ from the tubular configuration of support member 244 shown in FIGS. 9A-9C. FIGS. 10A-10C illustrate a portion of another example delivery system 260 that includes a stop tube 262, and which can be used to deploy stent 50. Stop tube 262 defines a longitudinal axis 264, which may be a longitudinal axis of both delivery system 260 and stop tube 262. FIG. 10A is a perspective view of a portion of delivery system 260, and illustrates an example retaining member 266 that defines a plurality of pockets 267A-267D and includes a plurality of support members 268A-268D, and FIG. 10B is an end view of the portion of the delivery system of FIG. 10A. FIG. 10C is a cross-sectional view of the portion of delivery system 260 of FIG. 10A, taken along line B-B of FIG. 10A and along longitudinal axis 264.

Stop tube 262 of delivery system 260 includes an outer wall 265 and a retaining member 266. Retaining member 266 defines pockets 267A, 267B, 267C, and 267D. Stop tube 262 further includes wall segments 270A, 270B, 270C, and 270D, which extend between corresponding ones of pockets 267A-267D and form portions of retaining member 266. Stop tube 262 further includes multiple support members 268A, 268B, 268C, and 268D that extend distally of corresponding ones of pockets 267A-267D, and defines a lumen 274 that may be configured to receive an inner member, such as inner member 18 of delivery system 10.

Many of the features of delivery system 260 may be substantially similar to the components of delivery system 10 of FIGS. 1, 3A, and 3B and to delivery system 230 of FIGS. 9A-9C. For example, example delivery system 260 may include inner member 18, sheath 14, and distal tip 22 of delivery system 10. In other examples, one or more of the features of delivery system 260 may be substantially similar to the components of delivery system 90 of FIGS. 4A-4C. In such examples, pockets 267A-267D of delivery system 260 may be formed in an outer wall of an inner member of delivery system 260, and delivery system 260 may include stop tube 96 of FIGS. 4A-4C. For the sake of brevity, however, delivery system 260 will be described as having pockets 267A-267D formed in outer wall 265 of stop tube 262.

The spacing, shapes, and dimensions of pockets 267A-267D may be substantially similar to those of pockets 234A-234D described above with respect to FIGS. 9A-9C, and will not be discussed again here. In addition, some aspects of support members 268A-268D also may be substantially similar to support member 244 of FIGS. 9A-9C. For example, support members 268A-268D may be formed integrally with stop tube 262, and may be extensions of stop tube 262 that are configured to be received radially within stent 50. In some examples, support members 268A-268D may extend distally within stent 50 past first row of cells 63 of when the stent 50 is received on inner member 18 and stop tube 262. In addition, support members 268A-268D each may have a thickness that is less than a thickness of a wall of stop tube 262, which may provide a gradual transition in stiffness between stop tube 262 and inner member 18. In some cases, this gradual transition in stiffness provided by support members 268A-268D may be advantageous to the operation of delivery system 260, as described above with respect to support member 53 of delivery system 10, and may allow a clinician to perform a medical procedure with greater ease and efficiency. For example, this gradual transition in stiffness may reduce or eliminate the possibility that stop tube 262 will kink at the end of retaining member 266. In this way, support members 268A-268D may provide stability to catheter 92, which may increase the navigability of delivery system 260 and improve the ease with which delivery system 260 may be advanced through the vasculature of a patient.

Support members 268A-268D each may have one or more of a variety of configurations. For example, one or more of support members 268A-268D may have blunt distal ends, as shown in FIGS. 10A and 10C. In other examples, one or more of support members 268A-268D may have rounded distal ends. In any such examples, one or more of support members 268A-268D may be tapered, such that a distal end of the one or more of support members 268A-268D is narrower than a proximal end of the one or more support members 268A-268D. In addition, support members 268A-268D may have one or more of a variety of lengths (e.g., relative to longitudinal axis 264). In some examples, each of support members 268A-268D may have the same length, whereas in other examples, one or more of support members 268A-268D may have a length that differs from one or more others of support members 268A-268D. In the example shown in FIG. 10A, one or more of support members 268A-268D may be substantially the same distance from longitudinal axis 264 from a proximal end to a distal end of the one or more support members 268A-268D, such that the one or more support members 268A-268D do not substantially curve inwardly toward or outwardly away from longitudinal axis 264. In other examples, one or more of support members 268A-268D may curve inwardly toward longitudinal axis 246, such that a distal end of the one or more support members 268A-268D may be closer to the longitudinal axis 246 than the proximal end of the one or more support members 268A-268D. In any such examples, the configurations of support members 268A-268D may be selected based on one or more considerations, such as a desired degree of support to be provided to stent 50 by support members 268A-268D.

Stop tube 262 of the delivery system 260 differs from stop tube 232 of delivery system 230 in the number and configuration of support members 268A-268D. That is, stop tube 262 includes multiple support members 268A-268D, spaced apart from one another, instead of a single tubular support member such as support member 244 of FIGS. 9A-9C.

Although the example of FIGS. 10A-10C illustrates stop tube 262 as including four support members 268A-268D, in other examples, stop tube 262 may include a greater or fewer number of support members. For example, stop tube 262 may include two support members positioned on opposite sides of the longitudinal axis 264 of stop tube 262 from one another (e.g., 268A and 268C). In addition, although the example of FIG. 10A illustrates that support members 268A-268D each extend from corresponding ones of pockets 267A-267D. In other examples, however, support members 268A-268D may be radially offset from pockets 267A-267D and extend from corresponding ones of wall segments 270A-270D. In some cases, it may be advantageous for a stop tube or inner member to include multiple support members, such as support members 268A-268D. For example, examples that include multiple support members may provide less of a difference in stiffness at a junction of a stop tube and an inner member than examples that include a single tubular support member, due to the space between the multiple support members. This may be desirable in some cases in which relatively less support is needed at the junction between a stop tube and an inner member. Such examples may include examples in which increased flexibility of a delivery system may be desirable and/or examples in which relatively less support at a junction of a stop tube and an inner member may protect one or more portions of a stent (e.g., connecting members of a stent) or a sheath of a delivery system by reducing an extent to which wear or friction may occur at such a junction.

The end view of stop tube 262 illustrated in FIG. 10B provides a view of stop tube 262 looking parallel with longitudinal axis 264 of stop tube from the distal ends of support members 268A-268D. Lumen 274 of stop tube 262 is shown in this view, as are each of pockets 267A-267D and wall segments 270A-270D. As shown in FIG. 10B, outer wall 265 of stop tube 262 may have a total thickness $T_T$. Each of pockets 267A-267D may extend through the outer wall 265 to a depth $D_R$. In the example of FIG. 10B, depth $D_R$ of pockets 267A-267D may be about 25% to about 75% of the total thickness $T_T$ of outer wall 265, although other depths of pockets 267A-267D are possible. Depth $D_R$ of pockets 267A-267D may be selected based on a thickness of one or more of connecting members 68A, 68B, 44A, and 44B of stent 50, thereby enabling pockets 267A-267D to securely receive one or more of connecting members 68A, 68B, 44A, and 44B. Because pockets 267A-267D each extend only partially through the thickness of outer wall 265, pockets 267A-267D each are partially defined by a corresponding floor 269A-269D formed by a material of outer wall 265, upon which one or more of connecting members 68A, 68B, 44A, and 44B may be supported when received within pockets 267A-267D. In some examples, one or more aspects of the configurations or dimensions of pockets 267A-267D, such as depth $D_R$ of pockets 267A-267D relative to connecting members 68A, 68B, 44A, and 44B of stent 50, may be substantially similar to the configurations and dimensions described above with respect to pockets 234A-234D of FIGS. 9A-9C, and will not be described again in detail here.

In some examples, depth $D_R$ of pockets 267A-267D may correspond to about 25% to about 100% of a thickness of one or more of connecting members 68A, 68B, 44A, and 44B of the stent 50. Depth $D_R$ of pockets 267A-267D may be selected based on a desired degree of security of the reception of connecting members 68A, 68B, 44A, and 44B within pockets 267A-267D, as described above with respect to FIGS. 9A-9C.

As also shown in FIG. 10B, support members 268A-268D of stop tube 262 may have a thickness $T_S$. Thickness $T_S$ of support members 268A-268D is less than total thickness $T_T$ of the outer wall 265 of stop tube 262 by depth $D_R$ of the pockets 267A-267D. In addition, a portion of outer wall 265 of stop tube 262 at pockets 267A-267D also may have thickness $T_S$, such that a floor of each of pockets 267A-267D forms a substantially continuous surface with an outer surface of a corresponding one of support members 268A-268D. As with pockets 234A-234D of FIGS. 9A-9C, the substantially continuous surface formed by the floors of pockets 267A-267D and the corresponding outer surfaces of support members 268A-268D may permit connecting members of stent 50 to be evenly received within pockets 267A-267D. The cross-sectional view of stop tube 262 shown in FIG. 10C illustrates the relationship between thickness $T_S$ of support members 268A-268D and total thickness $T_T$ of outer wall 265 of stop tube 262. As shown in FIG. 10C, thickness $T_S$ of support members 268A and 268B is less than total thickness $T_T$ of outer wall 265 of stop tube 262.

Figure 11A:
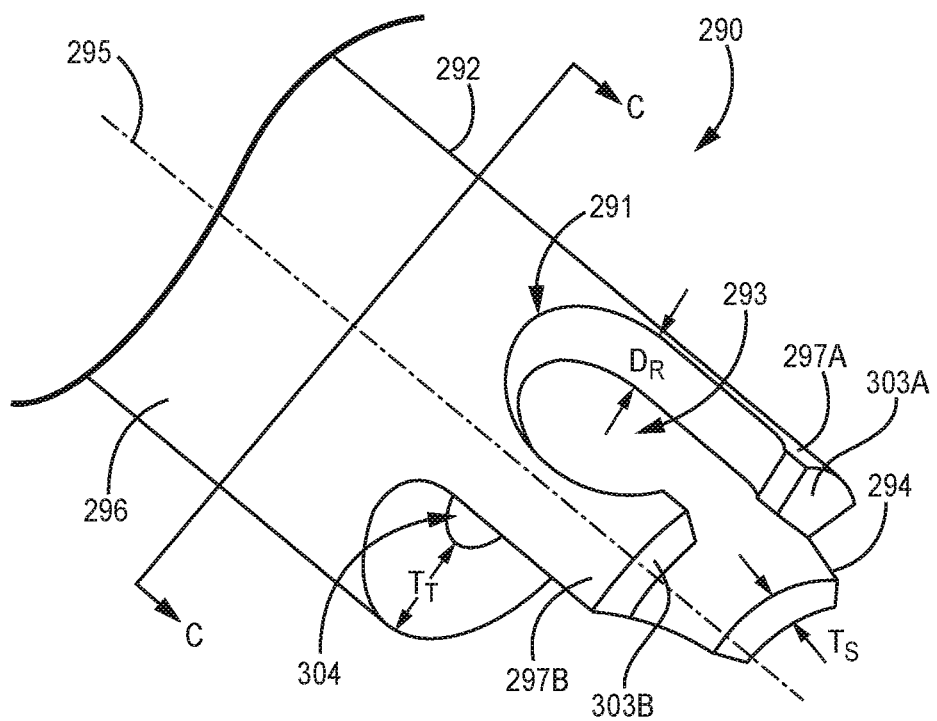
FIG. 11A is a perspective view of a portion of another example delivery system, and illustrates an example retaining member that defines a single pocket, where the delivery system includes a single support member.
Figure 11B:
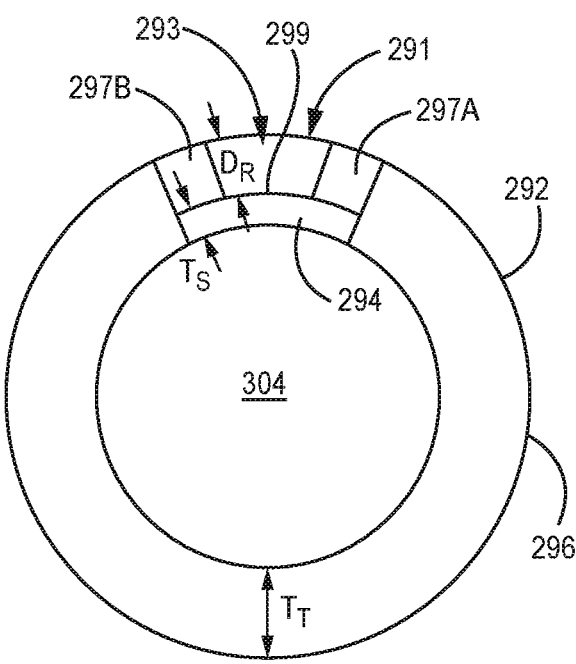
FIG. 11B is an end view of the portion of the delivery system of FIG. 11A.
Figure 11C:
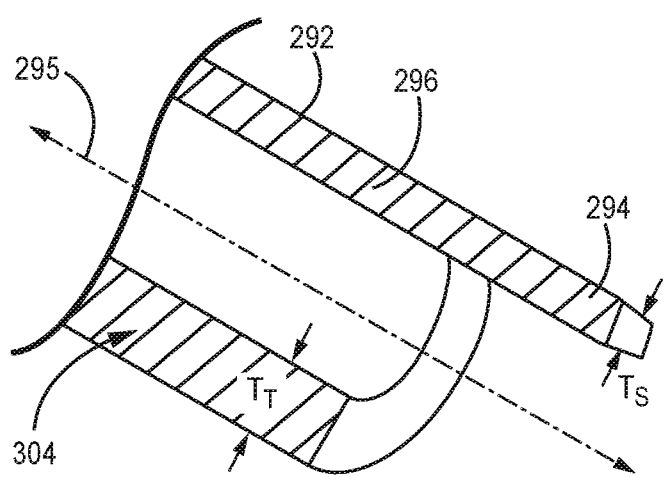
FIG. 11C is a cross-sectional perspective view of the portion of the delivery system of FIG. 11A, where the cross-section is taken along line C-C of FIG. 11A and along a longitudinal axis of the delivery system.

FIGS. 11A-11C illustrate a portion of another example delivery system 290 that can be used to deploy stent 50 and includes a stop tube 292. Stop tube 292 defines a longitudinal axis 295, which may be a longitudinal axis of both the delivery system 290 and stop tube 292. FIG. 11A is a perspective view of a portion of delivery system 290, and illustrates an example retaining member 291 that only defines a single pocket 293 and includes only a single support member 294, and FIG. 11B is an end view of the portion of delivery system 290 of FIG. 11A. FIG. 11C is a cross-sectional view of the portion of delivery system 290 of FIG. 11A, where the cross-section is taken along line C-C in FIG. 11A and along longitudinal axis 295.

Stop tube 292 includes an outer wall 296 having wall segments 297A, 297B that extend along an outer wall 296. Outer wall 296 of stop tube 292 includes retaining member 291, which defines pocket 293 recessed within a material of outer wall 296 and includes wall segments 297A and 297B. Wall segments 297A, 297B have respective distal ends 303A, 303B. In some examples, distal ends 303A, 303B of respective wall segments 297A, 297B may extend distally past a distal end of a lumen 304 that is defined by stop tube 292, as shown in FIG. 11A. Stop tube 292 further includes support member 294, which extends distally of retaining member 291 and pocket 293 and lumen 304, which may be configured to receive an inner member, such as inner member 18 of delivery system 10.

Many of the features of delivery system 290 may be substantially similar to the components of delivery system 10 of FIGS. 1-3B, delivery system 230 of FIGS. 9A-9C, and delivery system 260 of FIGS. 10A-10C. For example, example delivery system 290 may include inner member 18, sheath 14, and distal tip 22 of delivery system 10. In other examples, one or more of the features of delivery system 290 may be substantially similar to the components of delivery system 90 of FIGS. 4A-4C. In such examples, retaining member 291 and pocket 293 of delivery system 290 may be formed in an outer wall of an inner member of delivery system 290, and delivery system 290 may include stop tube 96 of FIGS. 4A-4C. For the sake of brevity, however, the delivery system 290 will be described with retaining member 291 and pocket 293 as being formed in outer wall 296 of stop tube 292.

The shape and dimensions of pocket 293 may be substantially similar to the shape and dimensions of individual ones of pockets 234A-234D described above with respect to FIGS. 9A-10C, and will not be discussed again here. In addition, some aspects of support member 294 also may be similar to support member 244 of FIGS. 9A-9C. For example, support member 294 may be formed integrally with stop tube 292, and may be at extension of stop tube 292 that is configured to be received radially within stent 50. In some examples, support member 294 may extend distally within stent 50 past first row of cells 63 when stent 50 is received on inner member 18 and the stop tube 292. In addition, support member 294 may have a thickness that is less than a thickness of a wall of stop tube 292, which may provide a gradual transition in stiffness between the stop tube 292 and the inner member 18. However, unlike support member 244, support member 294 shown in FIG. 9A is not tubular in shape, but instead may have a curved, semicircular shape in a cross-section taken orthogonal to longitudinal axis 295.

Although the example of FIG. 11A illustrates stop tube 292 as including a single pocket 293 and a single support member 294, in other examples, stop tube 292 may include two support members. For example, stop tube 292 may include a support member positioned on opposite sides of pocket 293 (e.g., one extending distally from each of wall segments 297A, 297B. In some cases, it may be advantageous for a stop tube or inner member to include a single pocket and only one or two support members, such as pocket 293 and support member 294. For example, stent 50 may include only one proximal connecting member, such as only one of connecting members 44A, 44B. In such examples, only a single pocket and a single, or in some examples two, support members may be needed to engage with stent 50. In some such examples having two support members, the second support member may help provide the gradual transition in stiffness between the stop tube 292 and the inner member 18, and/or may enable stent 50 to remain centered with respect to stop tube 292, which in turn may help one of connecting members 68A, 68B, 44A, or 44B of stent 50 to remain engaged with pocket 293 as delivery system 290 is advanced through patient vasculature to a treatment site.

The end view of stop tube 292 illustrated in FIG. 11B provides a view of stop tube 292 looking parallel with longitudinal axis 295 of the stop tube from a distal end 313 of support member 294. Lumen 304 of stop tube 292 is shown in this view, as are each of pocket 293 and wall segments 297A, 297B. As shown in FIGS. 11A and 11B, outer wall 296 of stop tube 292 may have a total thickness $T_T$, and the support member 294 may have a thickness $T_S$. Pocket 293 may extend through outer wall 296 to a depth $D_R$. In the example of FIG. 11B, depth $D_R$ of retaining member 226 may be about 25% to about 75% of the total thickness $T_T$ of outer wall 296, although other depths of pocket 293 are possible. Depth $D_R$ of pocket 293 may be selected based on a thickness of one or more of connecting members 68A, 68B, 44A, and 44B of stent 50, thereby enabling pocket 293 to securely receive one or more of connecting members 68A, 68B, 44A, and 44B. Because pocket 293 extends only partially through the thickness of outer wall 296, pocket 293 is partially defined by a floor 299 formed by a material of outer wall 296, upon which one or more of connecting members 68A, 68B, 44A, and 44B may be supported when received within pocket 293. In some examples, one or more aspects of the configurations or dimensions of the pocket 293, such as the depth $D_R$ of retaining member 226 relative to the connecting members 68A, 68B, 44A, and 44B of stent 50, may be substantially similar to the configurations and dimensions described above with respect to pockets 234A-234D of FIGS. 9A-9C, and will not be described again in detail here.

As also shown in FIG. 11B, support member 294 of stop tube 292 may have a thickness $T_S$. Thickness $T_S$ of support member 294 is less than total thickness $T_T$ of outer wall 296 of stop tube 292 by depth $D_R$ of retaining member 226. In addition, a portion of the outer wall 296 of stop tube 292 at pocket 293 also may have thickness $T_S$, such that a floor of pocket 293 forms a substantially continuous surface with an outer surface of support member 294. As with the pockets 234A-234D of FIGS. 9A-9C, the substantially continuous surface formed by the floor of pocket 293 and the outer surface of support member 294 may permit a connecting member of stent 50 to be evenly received within pocket 293, which may help stabilize stent 50 while stent 50 is received on stop tube 292. The end view of stop tube 292 shown in FIG. 11B illustrates the relationship between thickness $T_S$ of support member 294 and total thickness $T_T$ of outer wall 296 of stop tube 292. In the example illustrated in FIG. 11C, thickness $T_S$ of the support member 294 is less than total thickness $T_T$ of outer wall 296 of stop tube 292 by depth $D_R$ of pocket 293. However, in examples in which stop tube 292 includes two support members (e.g., one support member extending distally from each of wall segments 297A, 297B), each of the support members may have any thickness $T_S$ that is equal to or less than total thickness $T_T$ of stop tube 292.

Figure 12:
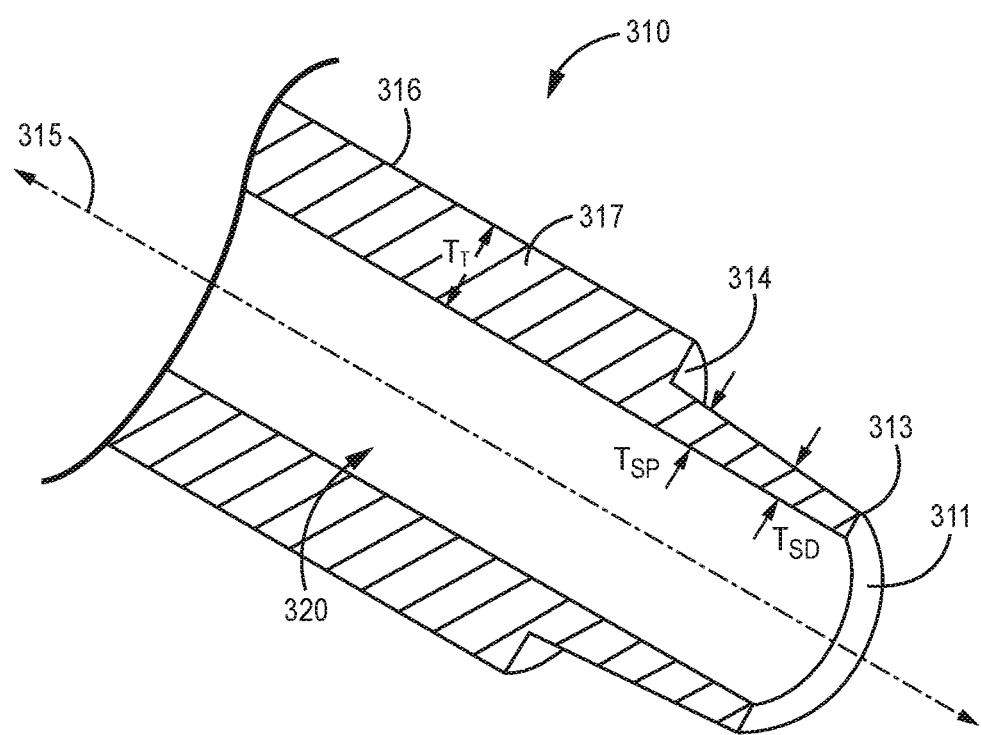
FIG. 12 is a cross-sectional perspective view of a portion of another example delivery system, where the delivery system includes a support member having a first thickness at a distal portion of the support member and a second thickness at a proximal portion of the support member, and where the cross-section is taken along a longitudinal axis of the delivery system.

FIG. 12 is a cross-sectional perspective view of a portion of another example delivery system 310, where a retaining member 311 of delivery system 310 includes a support member 312 having a first thickness $T_{SD}$ at a distal portion 313 of support member 312 and a second thickness $T_{SP}$ at a proximal end 314 of support member 312. The cross-sectional view of FIG. 12 is taken along a longitudinal axis 315 of delivery system 310, which also may be a longitudinal axis of stop tube 316. Stop tube 316 includes outer wall 317 having a thickness $T_T$, defines a lumen 320, and includes support member 312. One or more components of stop tube 316 may be substantially similar to the components of stop tube 232 described above with respect to FIGS. 10A-10C, and will not be discussed again in detail here. For example, support member 312 in the illustrated example of FIG. 12 may be a single support member having a tubular shape. In addition, although not visible in the cross-sectional view of FIG. 12, stop tube 316 may further include a retaining member, one or more pockets, and one or more wall segments, such as retaining member 233, one or more of pockets 234A-234D, and one or more of wall segments 242A-242D illustrated in FIGS. 9A-9C.

Stop tube 316 of delivery system 310 differs from stop tube 232 in that thickness $T_{SD}$ at a distal end 313 of support member 312 is different from thickness $T_{SP}$ at proximal end 314 of support member 312. For example, thickness $T_{SP}$ at proximal end 314 of support member 312 may be greater than thickness $T_{SD}$ at distal end 313 of support member 312 and lesser than thickness $T_{OW}$ of outer wall 317 of stop tube 232. In addition, the thickness of support member 312 may taper from the greater thickness $T_{SP}$ at proximal end 314 to lesser thickness $T_{SD}$ at distal end 313, such that the thickness of support member 312 is varied from proximal end 314 to distal end 313. The taper may be, for example, a linear taper from thickness $T_{SP}$ to thickness $T_{SP}$, or may be a non-linear taper, such as a step-wise transition between the thicknesses. Although support member 312 illustrated in FIG. 12 includes a tubular shape, support member 312 may have any suitable shape including, for example, any of the shapes of the support members illustrated in FIGS. 9A-11C.

The tapered thickness of support member 312 may provide a more gradual transition in stiffness between stop tube 316 and an inner member (e.g., inner member 18 of delivery system 10) than a support member having a constant thickness along its length. In some cases, the more gradual transition in stiffness provided by support member 312 may be advantageous to the operation of delivery system 310. For example, the gradual transition in stiffness provided by support member 312 may provide delivery system 310 with enhanced resistance to kinking at the junction of an inner member (e.g., inner member 18 of delivery system 10) and stop tube 316, thereby providing added stability to delivery system 310 and improving the ease with which delivery system 310 may be advanced through the vasculature of a patient.

Figure 13A:
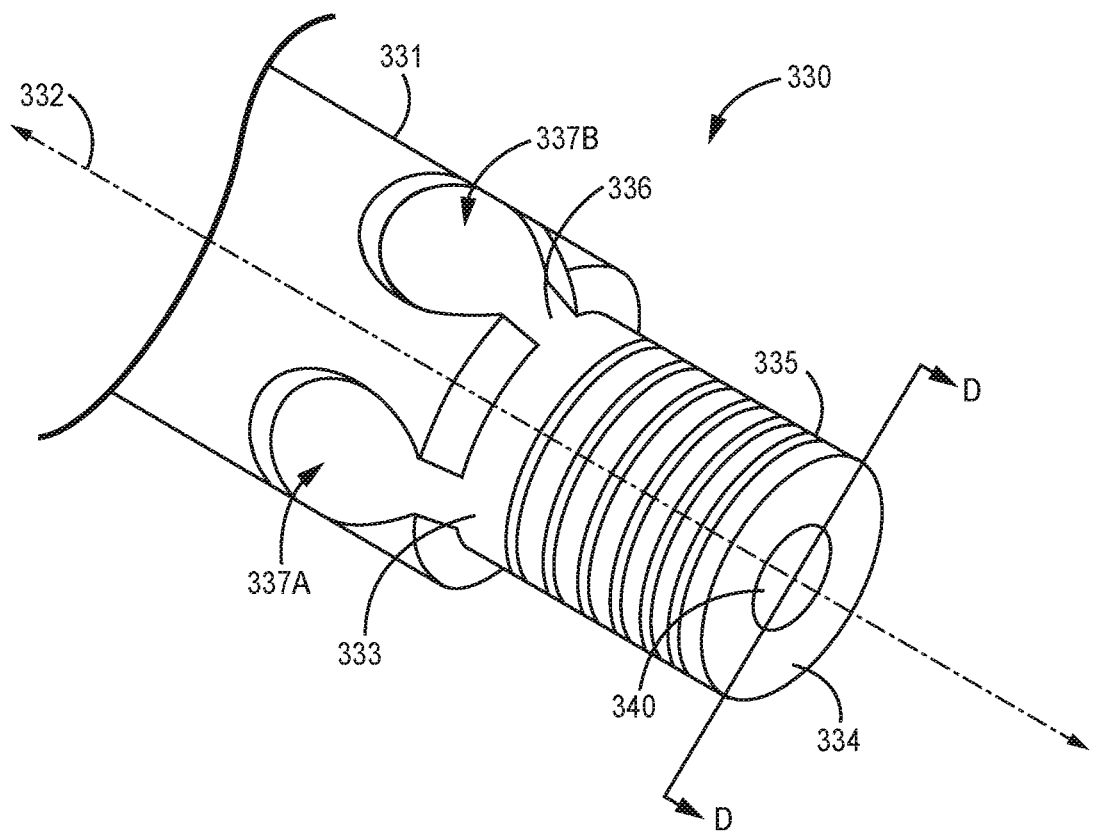
FIG. 13A is a perspective view of a portion of another example delivery system, where the delivery system includes a support member having a plurality of grooves spaced along an outer surface of the support member in a direction orthogonal to a longitudinal axis of the stop tube.
Figure 13B:
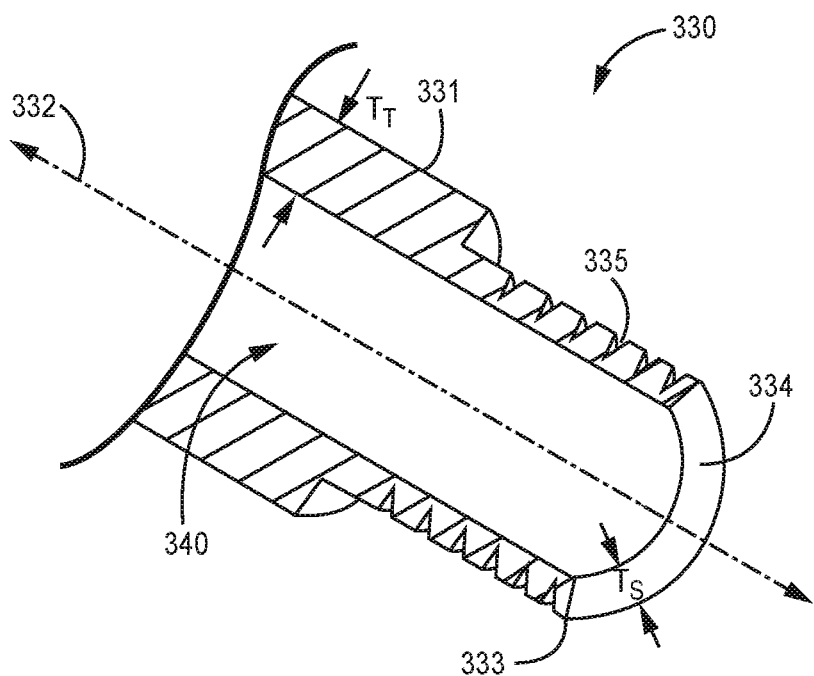
FIG. 13B is a cross-sectional view of the portion of the delivery system of FIG. 13A, where the cross-section is taken along line D-D of FIG. 13A and along the longitudinal axis of the delivery system.

FIGS. 13A and 13B illustrate a portion of another example delivery system 330 that can be used to deploy stent 50, and which includes a stop tube 331 that defines a longitudinal axis 332. FIG. 13A is a perspective view of a portion of delivery system 330, where stop tube 331 includes a support member 334 having a plurality of grooves 335 spaced along an outer surface 336 of support member 334 in a direction transverse (e.g., orthogonal) to a longitudinal axis 332 of stop tube 331. FIG. 13B is cross-sectional perspective view of a portion of stop tube 331 of delivery system 330 of FIG. 13A, where the cross-section is taken along line D-D in FIG. 13A and along longitudinal axis 332 of delivery system 330. Longitudinal axis 332 may be a longitudinal axis both of delivery system 330 and stop tube 331.

Stop tube 331 of delivery system 330 includes an outer wall 336, defines a lumen 340, and includes a support member 334, which extends distally past outer wall 336. Stop tube 336 defines pockets 337A and 337B, which may be substantially similar to any of the pockets described above with respect to the delivery systems of FIGS. 3A-12. For example, although two pockets 337A and 337B are illustrated in the example of FIG. 13A, in other examples, delivery system 330 may include a single pocket (e.g., pocket 337A or 337B), or may include additional pockets. As shown in the example of FIG. 13B, outer wall 336 of stop tube 331 has a total thickness $T_T$, and support member 334 has a thickness $T_S$, and includes outer surface 336. In the illustrated example, thickness $T_S$ of support member 334 is less than total thickness $T_T$ of outer wall 336 of stop tube 331. In some examples, support member 334 may be a segment of outer wall 336 of stop tube 331. One or more components of stop tube 331 may be substantially similar to the components of stop tube 232 described above with respect to FIGS. 9A-9C, and will not be discussed again in detail here. For example, support member 334 in the illustrated example of FIGS. 13A and 13B can be a single support member having a tubular shape.

Stop tube 331 of delivery system 330 differs from stop tube 232 in that support member 334 defines one or more grooves 335 that extend along outer surface 346 of support member 334. Each of grooves 335 may be an indentation or the like extending inward (e.g., radially inward in the case of a tubular support member 334) from outer surface 346 of support member 334 towards the lumen 340 (e.g., partially through thickness $T_S$ of support member 334). In the example of FIGS. 13A and 13B, grooves 335 extend along outer surface 346 of support member 334 axially about longitudinal axis 332. FIG. 13B illustrates an example of grooves 335 in which a cross-section of each of the grooves 335 (taken parallel to longitudinal axis 332) is generally V-shaped. In other examples, such a cross-section of each of grooves 335 may be generally U-shaped, semi-circular, or have any other suitable cross-sectional shape. Although support member 334 illustrated in FIGS. 13A and 13B includes a tubular shape, support member 334 may, in other examples, have any other suitable shape including, for example, any of the other configurations of the support members illustrated in FIGS. 10A-12.

As with the tapered thickness of support member 312 of delivery system 310 of FIG. 12, grooves 335 of support member 334 may provide a more gradual transition in stiffness between stop tube 331 and an inner member (e.g., the inner member 18 of the delivery system 10) that may be received within lumen 340 of stop tube 331 than a support member having a constant thickness. For example, as illustrated in FIG. 13A, a spacing between adjacent ones of grooves 335 may decrease in a proximal-to-distal direction along support member 334 parallel to longitudinal axis 332. The decreased spacing between adjacent ones of grooves 335 in a proximal-to-distal direction may increase the flexibility of the support member in the proximal-to-distal direction, thereby helping to render the transition in stiffness between stop tube 331 and an inner member more gradual. Grooves 335 thus may provide delivery system 330 with enhanced resistance to kinking and other potential advantages associated therewith. In some examples, support member 334 may include a tapered thickness similar to the tapered thickness of support member 312 of delivery system 310, in addition to grooves 335. In other examples, support members having a non-tubular shape, such as support members 268A-268D of delivery system 260 or support member 294 of delivery system 290 also may include one or more grooves 335.

Figure 14A:
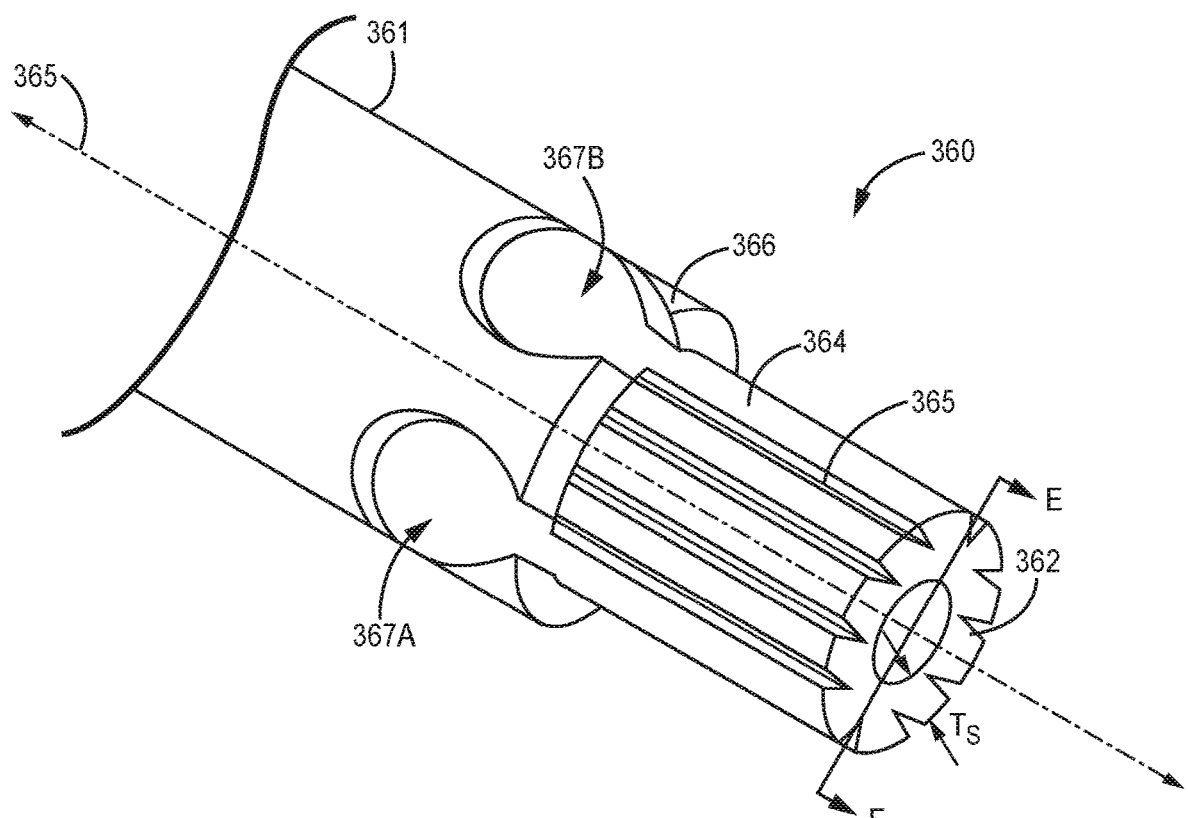
FIG. 14A is a perspective view of a portion of another example delivery system, where the delivery system includes a support member having a plurality of grooves spaced along an outer surface of the support member in a direction parallel to a longitudinal axis of the delivery system.
Figure 14B:
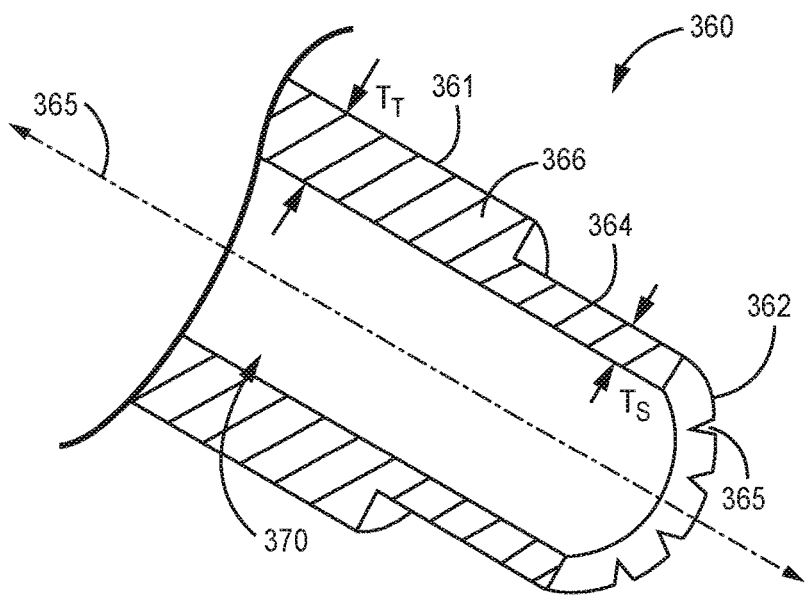
FIG. 14B is a cross-sectional view of the delivery system of FIG. 14A, where the cross-section is taken along line E-E of FIG. 14A and along the longitudinal axis of the delivery system.

FIGS. 14A and 14B illustrate another example delivery system 360 that can be used to deploy stent 50, and which includes a stop tube 361 that defines a longitudinal axis 365. FIG. 14A is a perspective view of a portion of delivery system 360, where a retaining member of delivery system 360 includes support member 362 having a plurality of grooves 363 spaced along an outer surface 364 of support member 362 in a direction parallel to a longitudinal axis 365 of stop tube 361. Stop tube 361 defines pockets 367A and 367B, which may be substantially similar to any of the pockets described above with respect to the delivery systems of FIGS. 3A-12. For example, although two pockets 367A and 367B are illustrated in the example of FIG. 13A, in other examples, delivery system 360 may include a single pocket (e.g., pocket 367A or 367B), or may include additional pockets. FIG. 14B is a cross-sectional perspective view of delivery system 360 of FIG. 14A, where the cross-section is taken along line E-E of FIG. 14A and along longitudinal axis 365 of delivery system 360. Longitudinal axis 365 may be a longitudinal axis both of delivery system 360 and stop tube 361.

Stop tube 361 of the illustrated example of delivery system 360 includes an outer wall 366 having a thickness $T_T$, defines a lumen 370, and includes an outer surface 364 and a support member 362 that extends distally past outer wall 366. One or more components of stop tube 361 may be substantially similar to the components of stop tube 232 described above with respect to FIGS. 9A-9C and stop tube 331 of FIGS. 13A and 13B, and will not be discussed again in detail here. For example, support member 362 in the illustrated example of FIGS. 14A and 14B is a single support member having a tubular shape, a thickness $T_S$, which may be less than total thickness $T_T$ of outer wall 366 of stop tube 361, and one or more grooves 363 defined in outer surface 364 of support member 362. In other examples, support members having a non-tubular shape, such as support members 268A-268D of delivery system 260 or support member 294 of delivery system 290 also may include one or more grooves.

In some examples, grooves 363 may be substantially similar to grooves 335 of support member 334 of delivery system 330. For example, each of the grooves 363 may be an indentation or the like extending inward (e.g., radially inward in the case of a tubular support member 362) from outer surface 364 of support member 362 towards lumen 370, partially through thickness $T_S$ of support member 362. In the example of FIGS. 14A and 14B, however, grooves 363 extend along outer surface 364 of support member 362 parallel to longitudinal axis 365. In some examples, grooves 363 defined in outer surface 364 of support member 362 may increase in width (e.g., a width measured orthogonal to longitudinal axis 365) in a proximal-to-distal direction, such that one or more of grooves 363 are wider at a distal portion of support member 362 than one or more of grooves 363 at a proximal portion of support member 362. Grooves 363 of support member 362 of delivery system 360 thus may provide similar advantages to those described with respect to grooves 335 of support member 334 of FIGS. 14A and 14B.

In any of the examples of FIGS. 13A-14B, grooves 335 and 376 may be formed in the respective outer surfaces 336 and 364 of support members 334 and 362 using any suitable technique, such as by laser etching, selective chemical dissolution, or by using a mechanical cutting technique. In the examples shown in FIGS. 13A-14B, grooves 335 and 376 continuously extend along respective outer surfaces 336 and 364 of support members 334 and 362. However, in other examples, one or more of grooves 335 and 376 may be discontinuous along a length of respective support members 334 and 362. That is, in such examples, grooves 335 and 376 may define perforations along the length of support members 334 and 362. The length of support members 334 and 362 is measured in a direction parallel to longitudinal axis 365. In addition to or instead of the discontinuous groove, in other examples, one or more of grooves 335 and 376 may extend along 50% to about 95% of the length of respective support members 334 and 362, such as about 70% to about 80%, or about 75% of the length of respective support members 334 and 362.

Figure 15:
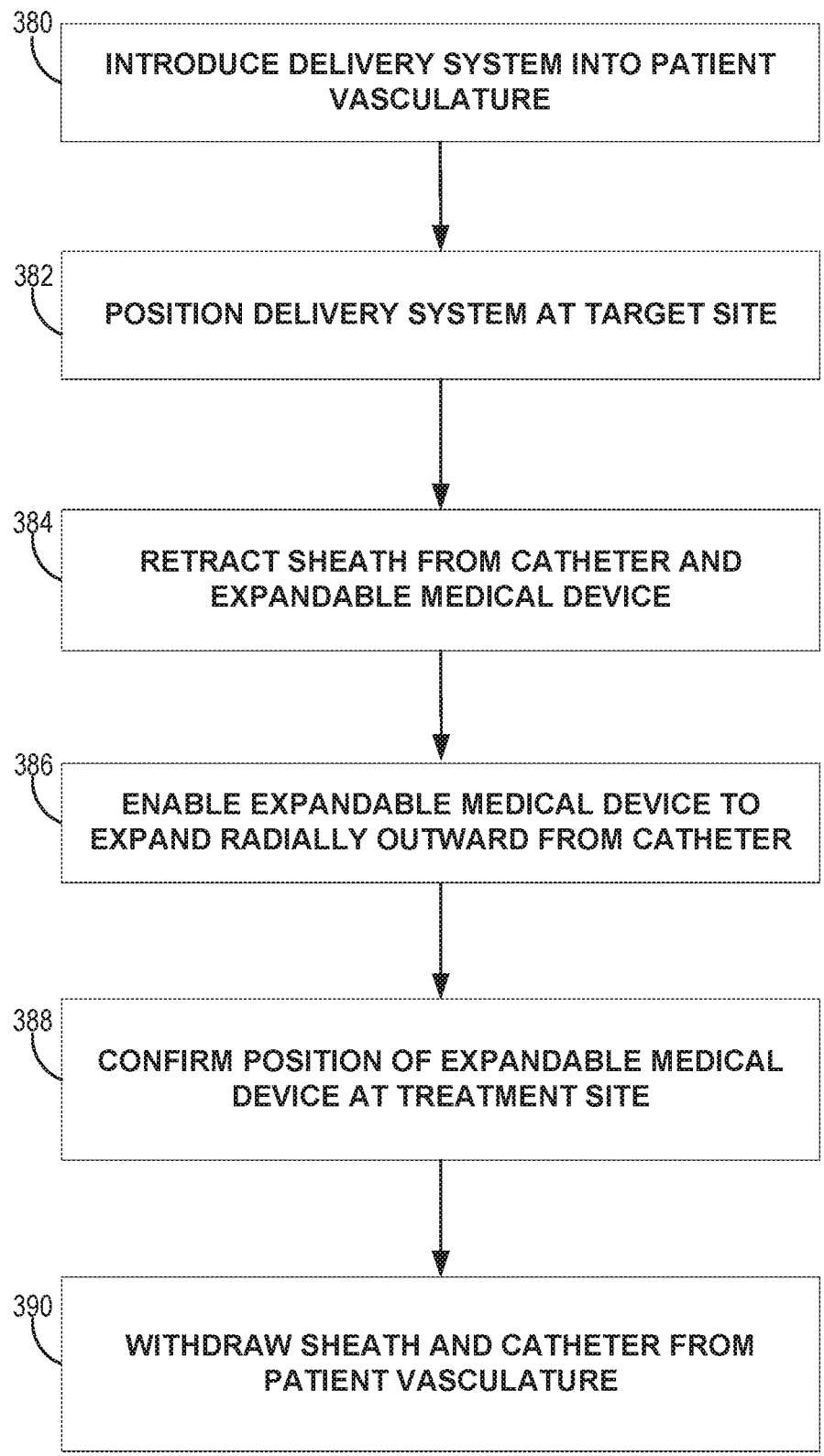
FIG. 15 is a flow diagram illustrating an example method of using any of the delivery systems described herein.

FIG. 15 is a flow diagram illustrating an example method of using any of delivery systems described herein. While the method shown in FIG. 15 is described with respect to delivery system 230 of FIGS. 9A-9C, in other examples, the method shown in FIG. 15 can be used with other delivery systems described herein, or with still other delivery systems configured to deliver and deploy an expandable medical device (e.g., a stent).

FIGS. 16A-16D are a series of cross-sectional views showing an example delivery system being operated in accordance with techniques described with respect to the example method of FIG. 15. For the sake of clarity, an inner member (e.g., inner member 18) that may be included with delivery system 230 is only shown in the view of FIGS. 16C and 16D, although in examples of FIGS. 16A and 16B, distal connecting members 68A, 68B of the stent 50, such as those shown in FIGS. 3A-5B, may be received within distal pockets 58A, 58B of inner member 18.

Figure 16A:
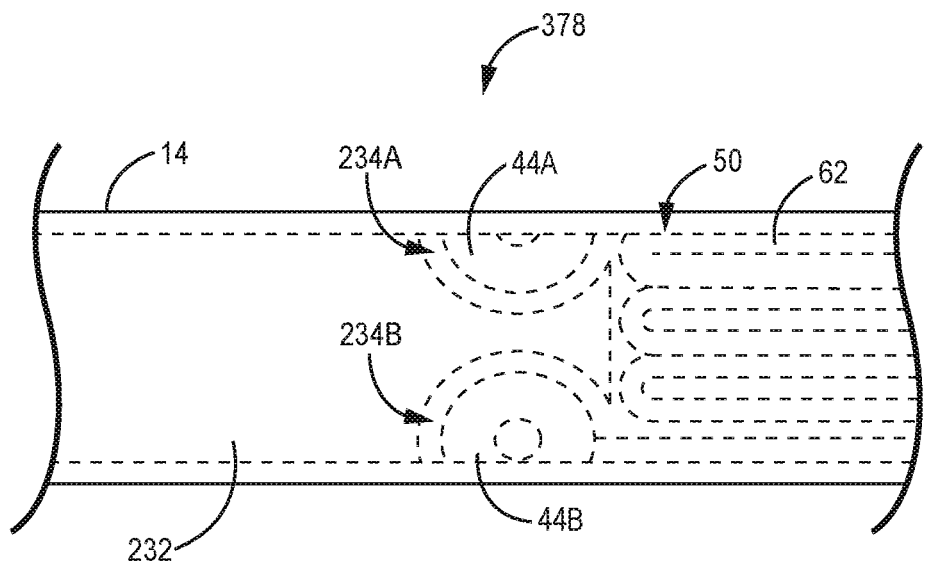
FIGS. 16A-16D are a series of cross-sectional views showing an example delivery system being operated in accordance with techniques described with respect to the example method of FIG. 15.

FIG. 16A shows a portion 378 of delivery system 230 positioned within a portion of the vasculature of a patient. Prior to the positioning of the delivery system shown in FIG. 16A, a clinician may create an insertion path from an entry point accessible from outside a patient to a target site within the vasculature, e.g., with the aid of a needle or another device having a cutting surface. The clinician may introduce a guidewire into the insertion path, e.g., through the needle or another device. Once the insertion path has been created, the clinician may introduce distal portion 378 of delivery system 230 into the insertion path over the guidewire, with proximal connecting members 44A, 44B of the stent 50 received in pockets 234A and 234B on stop tube 232 in the compressed configuration (e.g., with the struts 62 compressed) and with stop tube 232 received within sheath 14 (380).

Figure 16B:
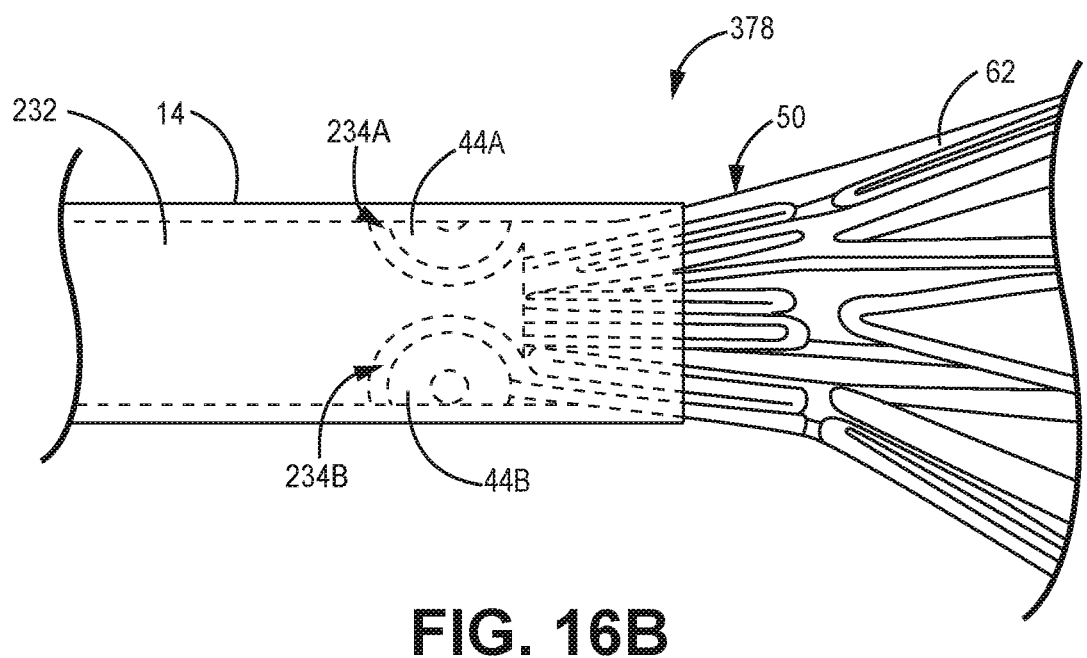

After introduction of distal portion 378 of the delivery system into the vasculature of the patient, the clinician then may advance distal portion 378 to a treatment site within a target vessel, such that stent 50 is positioned for deployment at the treatment site (382). Next, as shown in FIG. 16B, the clinician may begin to proximally retract sheath 14 from stent 50 and stop tube 232 (384). When sheath 14 is in the partially-retracted position illustrated in FIG. 16B (e.g., exposing a portion of stent 50 while still covering proximal connecting members 44A, 44B), the exposed portion of stent 50 may begin to expand such that a width of the exposed portion of stent 50 begins to increase from the collapsed stent diameter $S_{D1}$ described with respect to FIG. 3A toward expanded stent diameter $S_{D2}$ described with respect to FIG. 3B.

Figure 16C:
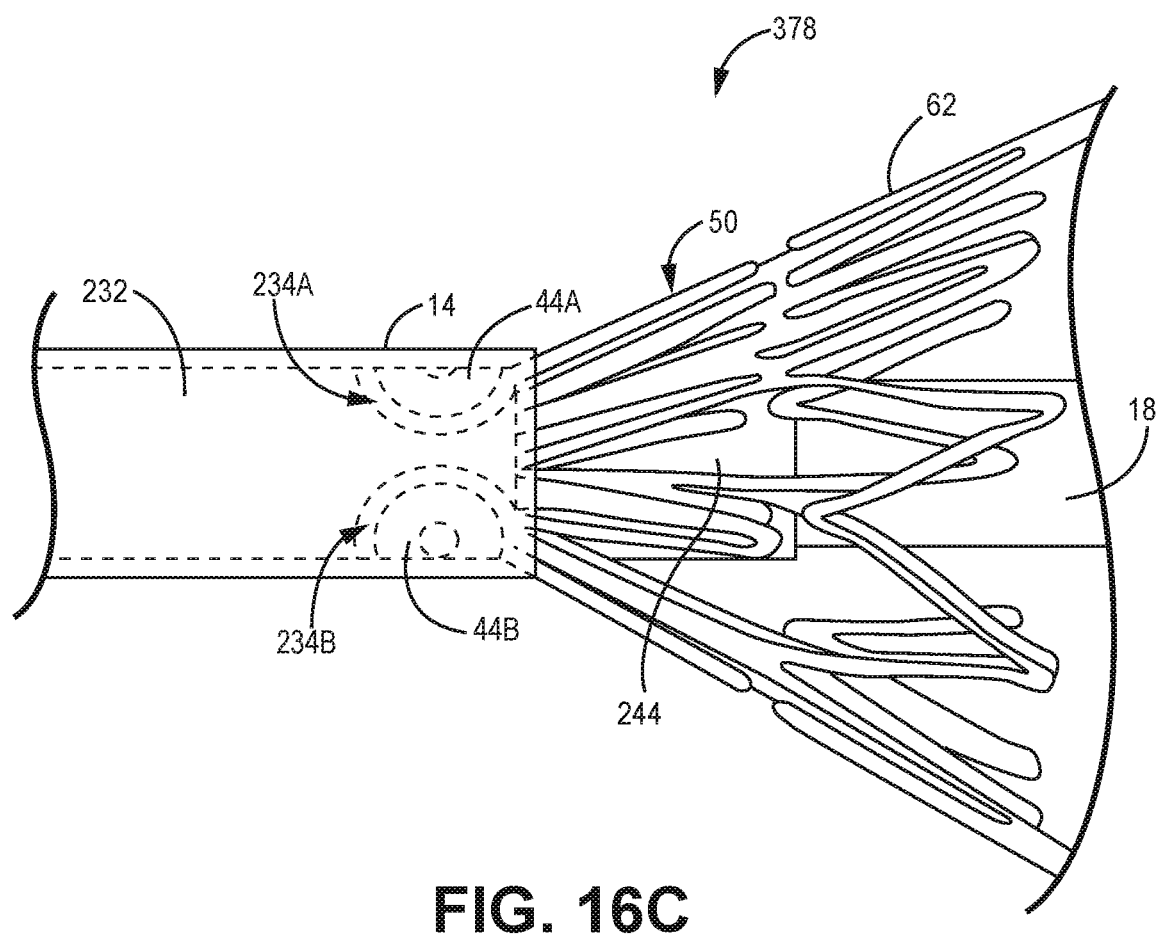
Figure 16D:
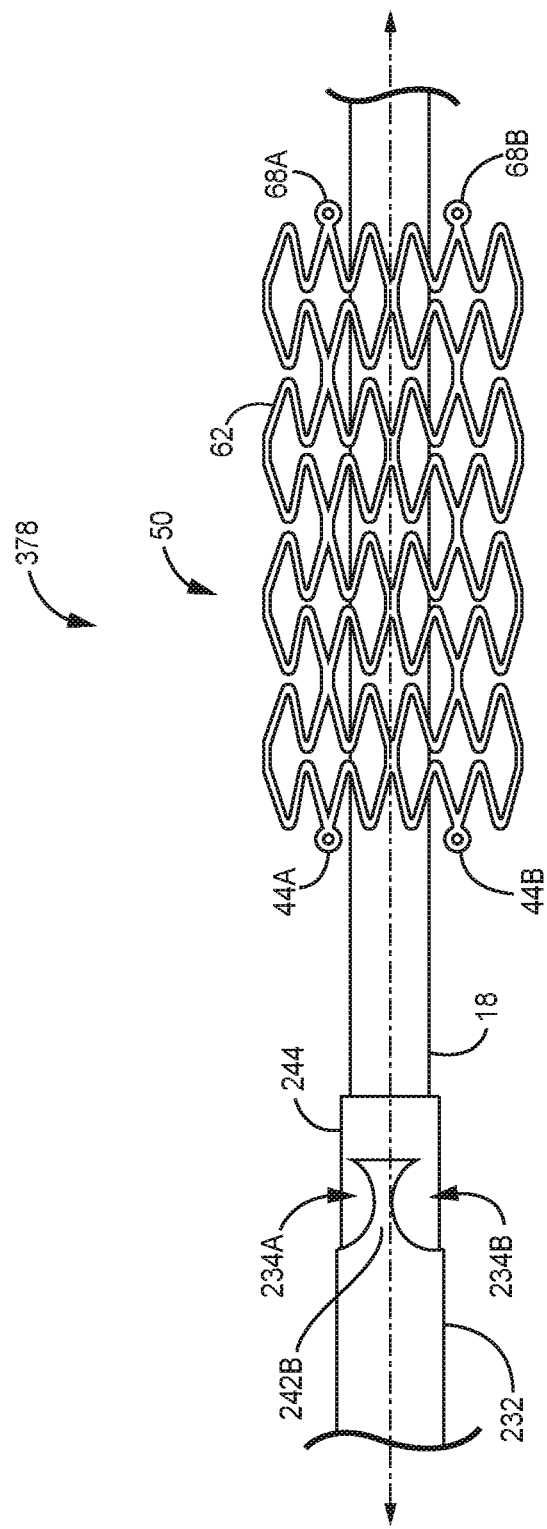

As the clinician continues to retract sheath 14 to expose more of stent 50, the width of the newly-exposed portion of stent 50 begins to increase from the collapsed stent diameter $S_{D1}$ toward expanded stent diameter $S_{D2}$, as shown in FIG. 16C. Although sheath 14 has been retracted nearly to proximal connecting members 44A, 44B of stent 50 in the example of FIG. 16C support member 244 of stop tube 232 remains within stent 50 and a portion of the stent 50 remains connected to stop tube 232 via proximal connecting members 44A, 44B. In this way, the clinician may maintain control over the placement of stent 50 within the target vessel until the clinician retracts sheath 14 proximally past proximal connecting members 44A, 44B. For example, if the clinician determines that stent 50 is not properly positioned at the target site during retraction of sheath 14, the clinician may distally advance sheath 14 to cover stent 50 and return stent 50 to the compressed configuration. Then, the clinician may advance or withdraw distal portion 378 of delivery system 230 to re-position stent 50 at the treatment site.

With the stent 50 positioned at the treatment site, the clinician then may proximally retract sheath 14 past the proximal connecting members 44A, 44B such that proximal connecting members 44A, 44B are exposed. When exposed, proximal connecting members 44A, 44B may disengage from the respective proximal retaining members. In examples in which stent 50 is a self-expanding stent, stent 50 may self-expand radially outward from stop tube 232 to assume the expanded configuration shown in FIG. 16D. In examples in which stent 50 is not a self-expanding stent (e.g., a stainless-steel stent), the clinician may cause stent 50 to assume the expanded configuration by inflating a balloon positioned within stent 50, or by any suitable technique. In any such examples, stent 50 may contact the inner surface of the wall of the target vessel at the treatment site when stent 50 is in an expanded configuration (386). The clinician then may confirm successful deployment of stent 50 at the treatment site by, for example, using an appropriate fluoroscopy, ultrasonic imaging, or MM-imaging technique (388). In some examples, stent 50 may include one or more of the radiopaque, ultrasonic, or MM-safe markers 45 described above with respect to FIGS. 6A-6N to aid in visualization by the clinician. Next, at some point after deploying stent 50 at the treatment site within the target vessel of the patient, the clinician then may withdraw stop tube 232 and sheath 14 from the vasculature of the patient (390).

The technique of FIG. 15 for delivering a medical device to a treatment site within a patient described herein may provide numerous advantages. For example, the example techniques described herein may save time during a given medical procedure over methods that employ a stent delivery system that does not include the support members and retaining members described herein. For example, the technique of FIG. 15 may reduce the potential for kinking of delivery system components while the delivery system is advanced through the vasculature of a patient and thus may provide one or more benefits, such as increased ease of use, reduced user fatigue, reduced patient discomfort, and an increase in efficiency of the treatment facility, among others.

Various aspects of the disclosure have been described. These and other aspects are within the scope of the following claims.

What is claimed is:

1. A catheter that defines a longitudinal axis, the catheter comprising:
    an inner member having an outer wall, wherein at least a portion of the inner member has a first stiffness;
    a retaining member defining a pocket configured to receive a connecting member of an expandable medical device, the retaining member having a second stiffness that is different from the first stiffness;
    a stop tube defining a lumen, wherein the inner member is received within the lumen of the stop tube; and
    a support member extending distally from the retaining member, wherein the support member is configured to be received radially within the expandable medical device when the connecting member is received within the retaining member, and wherein the support member is configured to provide a gradual transition between the first stiffness of the inner member and the second stiffness of the retaining member.

2. The catheter of claim 1, wherein the retaining member is formed in the outer wall of the inner member, and wherein the portion of the inner member having the first stiffness is distal to or proximal to the retaining member, wherein the pocket extends through about 25% to about 75% of a thickness of the outer wall of the inner member.

3. The catheter of claim 1, wherein the retaining member defining a pocket is a proximal retaining member defining a proximal pocket and the connecting member is a proximal connecting member of the expandable medical device, the catheter further comprising a distal retaining member distal to the proximal retaining member, the distal retaining member defining a distal pocket being configured to receive a distal connecting member of the expandable medical device.

4. The catheter of claim 3, wherein the support member is a proximal support member, the catheter further comprising a distal support member extending proximally from the distal retaining member.

5. The catheter of claim 1, wherein the retaining member is formed in the stop tube.

6. The catheter of claim 5, wherein the pocket extends through about 25% to about 75% of a thickness of an outer wall of the stop tube.

7. The catheter of claim 1, wherein the support member extends distally of the retaining member and is radially offset from the pocket of the retaining member with respect to the longitudinal axis of the catheter.

8. The catheter of claim 1, wherein the support member comprises a tubular support member.

9. The catheter of claim 1, wherein the retaining member defines a plurality of pockets, and each of the plurality of pockets is configured to receive a respective connecting member of a plurality of connecting members of the expandable medical device.

10. The catheter of claim 9, wherein the support member comprises a plurality of support members, and wherein a corresponding support member of the plurality of support members extends distally from each pocket of the plurality of pockets.

11. The catheter of claim 1, wherein the retaining member defines only one pocket.

12. The catheter of claim 1, wherein the catheter includes only one support member.

13. The catheter of claim 1, wherein a surface of the support member defines at least one groove.

14. A catheter that defines a longitudinal axis, the catheter comprising:
    an inner member having an outer wall, wherein at least a portion of the inner member has a first stiffness;
    a retaining member defining a pocket configured to receive a connecting member of an expandable medical device, the retaining member having a second stiffness that is different from the first stiffness, wherein the retaining member is formed in the outer wall of the inner member, wherein the portion of the inner member having the first stiffness is distal to or proximal to the retaining member, and wherein the pocket extends through about 25% to about 75% of a thickness of the outer wall of the inner member; and
    a support member extending distally from the retaining member, wherein the support member is configured to be received radially within the expandable medical device when the connecting member is received within the retaining member, and wherein the support member is configured to provide a gradual transition between the first stiffness of the inner member and the second stiffness of the retaining member.

15. The catheter of claim 14, wherein at least a portion of the support member has a thickness that is less than the thickness of the outer wall of the inner member.

16. The catheter of claim 14, wherein the retaining member defining a pocket is a proximal retaining member defining a proximal pocket and the connecting member is a proximal connecting member of the expandable medical device, the catheter further comprising a distal retaining member distal to the proximal retaining member, the distal retaining member defining a distal pocket being configured to receive a distal connecting member of the expandable medical device.

17. A delivery system comprising:
an expandable medical device having a proximal end and a distal end, the proximal end of the expandable medical device including a connecting member;
a catheter defining a longitudinal axis, the catheter comprising:
an inner member having an outer wall, wherein at least a portion of the inner member has a first stiffness;
a retaining member defining a pocket configured to receive the connecting member of the expandable medical device, the retaining member having a second stiffness that is different from the first stiffness;
a stop tube defining a lumen, wherein the inner member is received within the lumen of the stop tube; and
a support member extending distally from the retaining member, wherein the support member is configured to be received radially within the expandable medical device when the connecting member is received within the retaining member, and wherein the support member is configured to provide a gradual transition between the first stiffness of the inner member and the second stiffness of the retaining member; and
a sheath mounted about the catheter and configured for longitudinal movement relative to the catheter.

18. The delivery system of claim 17, wherein the expandable medical device comprises a plurality of struts that form a plurality of cells.

19. The delivery system of claim 18, wherein the support member extends distally of a proximal-most row of cells of the plurality of cells when the connecting member is received within the pocket.

20. The delivery system of claim 17, wherein the retaining member is formed in the outer wall of the inner member, and wherein the portion of the inner member having the first stiffness is distal to or proximal to the retaining member.

21. The delivery system of claim 20, wherein the pocket extends through about 25% to about 75% of a thickness of the outer wall of the inner member.

22. The delivery system of claim 17, wherein the retaining member defining a pocket is a proximal retaining member defining a proximal pocket and the connecting member is a proximal connecting member of the expandable medical device, the catheter further comprising a distal retaining member distal to the proximal retaining member, the distal retaining member defining a distal pocket being configured to receive a distal connecting member of the expandable medical device.

23. The delivery system of claim 17, wherein the retaining member is formed in the stop tube.

24. The delivery system of claim 17, wherein the retaining member defines a plurality of pockets, and each of the plurality of pockets is configured to receive a respective connecting member of a plurality of connecting members of the expandable medical device.

25. The delivery system of claim 17, wherein the support member comprises a plurality of support members, and wherein a corresponding support member of the plurality of support members extends distally from each pocket of the plurality of pockets.

26. The delivery system of claim 17, wherein a surface of the support member defines at least one groove.

27. A method comprising:
introducing a delivery system into a vessel of a patient, the delivery system comprising:
an expandable medical device having a proximal end and a distal end, the proximal end of the expandable medical device including a connecting member;
a catheter defining a longitudinal axis, the catheter comprising:
an inner member having an outer wall, wherein at least a portion of the inner member has a first stiffness;
a retaining member defining a pocket configured to receive the connecting member of the expandable medical device, the retaining member having a second stiffness that is different from the first stiffness;
a stop tube defining a lumen, wherein the inner member is received within the lumen of the stop tube; and
a support member extending distally from the retaining member, wherein the support member is configured to be received radially within the expandable medical device when the connecting member is received within the retaining member, and wherein the support member is configured to provide a gradual transition between the first stiffness of the inner member and the second stiffness of the retaining member; and
a sheath mounted about the catheter and adapted for longitudinal movement relative to the catheter; and
withdrawing the sheath from the catheter to release the expandable medical device from the delivery system.

28. The method of claim 27, wherein the expandable medical device comprises a plurality of struts that form a plurality of cells.

29. The method of claim 28, wherein the support member extends distally of a proximal-most row of cells of the plurality of cells when the connecting member is received within the pocket.

30. The method of claim 27, wherein the retaining member defines a plurality of pockets, and each of the plurality of pockets is configured to receive a respective connecting member of a plurality of connecting members of the expandable medical device.

* * * * *